US008871711B2

(12) United States Patent
Cotsarelis et al.

(10) Patent No.: US 8,871,711 B2
(45) Date of Patent: Oct. 28, 2014

(54) FIBROBLAST GROWTH FACTOR-9 PROMOTES HAIR FOLLICLE REGENERATION AFTER WOUNDING

(75) Inventors: George Cotsarelis, Berwyn, PA (US); Oh Sang Kwon, Seoul (KR)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 276 days.

(21) Appl. No.: 13/129,100

(22) PCT Filed: Nov. 11, 2009

(86) PCT No.: PCT/US2009/064049
§ 371 (c)(1),
(2), (4) Date: Aug. 2, 2011

(87) PCT Pub. No.: WO2010/056759
PCT Pub. Date: May 20, 2010

(65) Prior Publication Data
US 2011/0282267 A1 Nov. 17, 2011

Related U.S. Application Data

(60) Provisional application No. 61/114,028, filed on Nov. 12, 2008.

(51) Int. Cl.
*A61K 38/17* (2006.01)
*A61M 37/00* (2006.01)
*A61P 17/14* (2006.01)
*A61Q 7/00* (2006.01)
*A61K 8/64* (2006.01)
*A61K 38/18* (2006.01)

(52) U.S. Cl.
CPC ... *A61Q 7/00* (2013.01); *A61K 8/64* (2013.01); *A61K 38/1825* (2013.01); *Y10S 514/88* (2013.01)
USPC .............. 514/9.1; 514/20.7; 514/880; 604/20

(58) Field of Classification Search
None
See application file for complete search history.

(56) References Cited

U.S. PATENT DOCUMENTS

| 7,175,842 | B2 | 2/2007 | Morgan et al. | |
|---|---|---|---|---|
| 2005/0095706 | A1* | 5/2005 | Zhang et al. | 435/368 |
| 2007/0092496 | A1 | 4/2007 | Zheng et al. | |
| 2007/0122387 | A1 | 5/2007 | Cochran et al. | |
| 2007/0233038 | A1 | 10/2007 | Pruitt et al. | |
| 2007/0243132 | A1 | 10/2007 | Russel-Jones et al. | |
| 2007/0299032 | A1 | 12/2007 | Ehama | |
| 2008/0193423 | A1 | 8/2008 | Brunton et al. | |

FOREIGN PATENT DOCUMENTS

| EP | 0455422 | 6/1991 |
|---|---|---|
| GB | 2321852 | 8/1998 |
| JP | 2003192541 A | 7/2003 |
| WO | WO01/74164 A | 10/2001 |
| WO | WO 2006/105109 A1 | 10/2006 |

OTHER PUBLICATIONS

Cardoso et al. Retinoic acid alters the expression of pattern-related genes in the developing rat lung. Dev Dyn. Sep. 1996;207(1):47-59.*
Andl et al., WNT Signals are Required for the Initiation of Hair Follicle Development, Developmental Cell, May 2002, vol. 2, pp. 643-653.
Chiang et al., Essential Role for Sonic Hedgehog During Hair Follicle Morphogenesis, Developmental Biology, 1999, vol. 205, pp. 1-9.
Huelsken et al., β-Catenin Controls Hair Follicle Morphogenesis and Stem Cell Differentiation in the Skin, Cell, May 18, 2001, vol. 105, pp. 533-545.
Ito et al., Wnt-dependent de novo Hair Follicle Regeneration in Adult Mouse Skin After Wounding, Nature Publishing Group, May 2007, vol. 447, pp. 316-.
Millar et al., Molecular Mechanisms Regulating Hair Follicle Development, The Society for Investigative Dermatology, Inc., Feb. 2, 2002, vol. 118, pp. 216-225.
Silva-Vargas et al., β-Catenin and Hedgehog Signal Strength can Specify Number and Location of Hair Follicles in Adult Epidermis without Recruitment of Bulge Stem Cells, Developmental Cell, Jul. 2005, vol. 9, pp. 121-131.
Argyris, "Tumor promotion by abrasion induced epidermal hyperplasia in the skin of mice." Journal of Investigative Dermatology 75.4, pp. 360-362 (1980).
Bianchi et al. "Exploiting the keratin 17 gene promoter to visualize live cells in epithelial appendages of mice." Molecular and cellular biology 25.16, pp. 7249-7259 (2005).
Diamond et al. "Conditional gene expression in the epidermis of transgenic mice using the tetracycline-regulated transactivators tTA and rTA linked to the keratin 5 promoter." Journal of Investigative Dermatology 115.5, pp. 788-794 (2000).
Komi-Kuramochi et al., "Expression of fibroblast growth factors and their receptors during full-thickness skin wound healing in young and aged mice". Journal of Endocrinology. vol. 186. No. 2.; pp. 273-289 (Aug. 2005).
Kwon et al., "Fibroblast growth factor 9 from dendritic epidermal T cells promotes hair follicle neogenesis after wounding in adult skin". Journal of Investigative Dermatology. vol. 129. No. Supp 1. 1. p. S104 (Apr. 2009).
Lee et al. "A critical role for Dnmt1 and DNA methylation in T cell development, function, and survival." *Immunity* 15.5, pp. 763-774 (2001).
White et al. "FGF9 and SHH signaling coordinate lung growth and development through regulation of distinct mesenchymal domains." *Development* 133.8, pp. 1507-1517 (2006).

* cited by examiner

*Primary Examiner* — David Romeo
(74) *Attorney, Agent, or Firm* — Mark S. Cohen; Pearl Cohen Zedek Latzer Baratz LLP

(57) ABSTRACT

The present invention provides methods for treating hair loss, treating, inhibiting, or suppressing a degenerative skin disorder, treating androgenetic alopecia (AGA), generating new hair follicles (HF), and increasing the size of existing HF. The methods comprise epidermal disruption or administration of wnt, and administration of a fibroblast growth factor-9 polypeptide or another compound that upregulates sonic hedgehog gene signaling.

88 Claims, 16 Drawing Sheets

γδTCR immunostaining of regenerated epidermis (SD7, wholemount) ×200

FGF9 immunostaining of SD1 sample (frozen section) ×400

δγTCR & FGF9 for SD1 sample

γδTCR

FGF9

γδTCR & FGF9

γδTCR & FGF9 for E14 embryonic skin

γδTCR

FGF9

γδTCR & FGF9

A.

- Treatment schedule with 3 week-old C57BL/6 mice
  - subepidermal injection: 50 μl of 10 μg/ml anti-FGF9 or IgG2a isotype control
  - SD1-SD4, tissue sampling at SD5

B.

C.

Mean ± SD. * : $P < 0.05$, ** : $< 0.01$, compared to control

Dermis: Alkaline phosphatase staining

Epidermis: K17 staining

Dermis: Alkaline phosphatase staining

FIBROBLAST GROWTH FACTOR-9 PROMOTES HAIR FOLLICLE REGENERATION AFTER WOUNDING

CROSS-REFERENCE TO RELATED APPLICATIONS

This application is a National Phase Application of PCT International Application PCT/US09/64049, filed Nov. 12, 2009 that claims priority to U.S. Provisional Application 61/114,028, filed Nov. 12, 2008, both of which are incorporated by reference herein in their entirety.

GOVERNMENT INTEREST STATEMENT

This invention was made in whole or in part with government support under Grant Number NIH/NIAMS AR46837, awarded by the National Institutes of Health. The United States government may have certain rights in the invention.

FIELD OF THE INVENTION

The invention relates to pharmaceutical compositions and methods for treating hair loss and regenerating hair follicles. Specifically, the invention relates to fibroblast growth factor-9 polypeptides and administering a fibroblast growth factor-9 polypeptide for treating hair loss or regenerating hair follicles.

BACKGROUND OF THE INVENTION

Follicular neogenesis is defined as the generation of new hair follicles (HF) after birth. Humans are born with a full complement of HF, which can change in size and growth characteristics as in early baldness or can ultimately degenerate and disappear as in late stages of baldness or in permanent scarring (cicatricial) alopecias. Therefore, the generation of new HF is desirable in the treatment of common baldness as well as less common hair loss conditions, such as discoid lupus erythematosis, congenital hypotrichosis, lichen planopilaris and other scarring alopecias.

SUMMARY OF THE INVENTION

The present invention provides methods of treating hair loss, treating, inhibiting, or suppressing a degenerative skin disorder, and treating androgenetic alopecia (AGA) in a subject and generating new hair follicles (HF) and increasing the size of existing HF, comprising epidermal disruption or administration of wnt, and administration of a fibroblast growth factor-9 polypeptide or another compound that upregulates sonic hedgehog gene signaling.

Thus, in one embodiment, the present invention provides a method of treating hair loss in a subject comprising the steps of (a) disrupting the epidermis in the region of said hair loss in said subject and (b) administering a composition comprising a fibroblast growth factor-9 to polypeptide to said subject.

In one embodiment, the hair loss is due to androgenetic alopecia (AGA). In one embodiment, the AGA is male pattern baldness. In another embodiment, the AGA is female pattern baldness. In one embodiment, the hair loss is the result of a skin injury. In one embodiment, the hair loss is in the scalp or eyebrow of said subject. In one embodiment, the hair loss is in scarred skin tissue of said subject. In one embodiment, the step of administering is performed 3-12 days after said step of disrupting. In one embodiment, the step of disrupting is performed by exposing the region of said hair loss to a mechanical, chemical, or optical stimulus. In one embodiment, the optical stimulus is radiation. In one embodiment, the administering step is via topical administration. In another embodiment, the administering step is via subepidermal administration.

In another embodiment, the present invention provides a method for generating a hair follicle in the dermis of a subject with hair loss comprising the steps of (a) disrupting the epidermis in the region of said hair loss in said subject and (b) administering a composition comprising a fibroblast growth factor-9 polypeptide to said subject.

In another embodiment, the present invention provides a method for increasing the size of a hair follicle in the dermis of a subject with hair loss comprising the steps of (a) disrupting the epidermis in the region of said hair loss in said subject and (b) administering a composition comprising a fibroblast growth factor-9 polypeptide to said subject.

In another embodiment, the present invention provides a method for increasing hair follicle formation in the skin of a subject with hair loss comprising the steps of (a) disrupting the epidermis in the region of said hair loss in said subject and (b) administering a composition comprising a fibroblast growth factor-9 polypeptide to said subject.

In another embodiment, the present invention provides a method for treating, inhibiting, or suppressing a degenerative skin disorder comprising the steps of (a) disrupting the epidermis in the region of said degenerative skin disorder in said subject and (b) administering a composition comprising a fibroblast growth factor-9 polypeptide to said subject.

In another embodiment, the present invention provides a method for treating an androgenetic alopecia (AGA) in a scalp of a subject comprising the steps of (a) disrupting the epidermis in the region of said AGA in said subject and (b) administering a composition comprising a fibroblast growth factor-9 polypeptide to said subject.

In another embodiment, the present invention provides a method of treating hair loss in a subject comprising the step administering a composition comprising a fibroblast growth factor-9 polypeptide and a wnt polypeptide to said subject.

In another embodiment, the present invention provides a method for generating a hair follicle in the dermis of a subject comprising the step of administering a composition comprising a fibroblast growth factor-9 polypeptide and a wnt polypeptide to said subject.

In another embodiment, the present invention provides a method for increasing the size of a hair follicle in the dermis of a subject comprising the step of administering a composition comprising a fibroblast growth factor-9 polypeptide and a wnt polypeptide to said subject.

In another embodiment, the present invention provides a method for increasing hair follicle formation in the skin of a subject comprising the step of administering a composition comprising a fibroblast growth factor-9 polypeptide and a wnt polypeptide to said subject.

In another embodiment, the present invention provides a method for treating, inhibiting, or suppressing a degenerative skin disorder comprising the step of administering a composition comprising a fibroblast growth factor-9 polypeptide and a wnt polypeptide to said subject.

In another embodiment, the present invention provides a method for treating an androgenetic alopecia (AGA) in a scalp of a subject comprising the step of administering a composition comprising a fibroblast growth factor-9 polypeptide and a wnt polypeptide to said subject.

In another embodiment, the present invention provides a method of treating hair loss in a subject comprising the steps of (a) disrupting the epidermis in the region of said hair loss in said subject and (b) administering a composition comprising a compound or factor that upregulates sonic hedgehog (SHH) to said subject.

In another embodiment, the present invention provides a method for generating a hair follicle in the dermis of a subject comprising the steps of (a) disrupting the epidermis in the region of said hair loss in said subject and (b) administering a composition comprising a compound or factor that upregulates sonic hedgehog (SHH) to said subject.

In another embodiment, the present invention provides a method for increasing the size of a hair follicle in the dermis of a subject comprising the steps of (a) disrupting the epidermis in the region of said hair loss in said subject and (b) administering a composition comprising a compound or factor that upregulates sonic hedgehog (SHH) to said subject.

In another embodiment, the present invention provides a method for increasing hair follicle formation in the skin of a subject comprising the steps of (a) disrupting the epidermis in the region of said hair loss in said subject and (b) administering a composition comprising a compound or factor that upregulates sonic hedgehog (SHH) to said subject.

In another embodiment, the present invention provides a method for treating, inhibiting, or suppressing a degenerative skin disorder comprising the steps of (a) disrupting the epidermis in the region of said hair loss in said subject and (b) administering a composition comprising a compound or factor that upregulates sonic hedgehog (SHH) to said subject.

In another embodiment, the present invention provides a method for treating an androgenetic alopecia (AGA) in a scalp of a subject comprising the steps of (a) disrupting the epidermis in the region of said hair loss in said subject and (b) administering a composition comprising a compound or factor that upregulates sonic hedgehog (SHH) to said subject.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE PRESENT INVENTION

Figure 1:
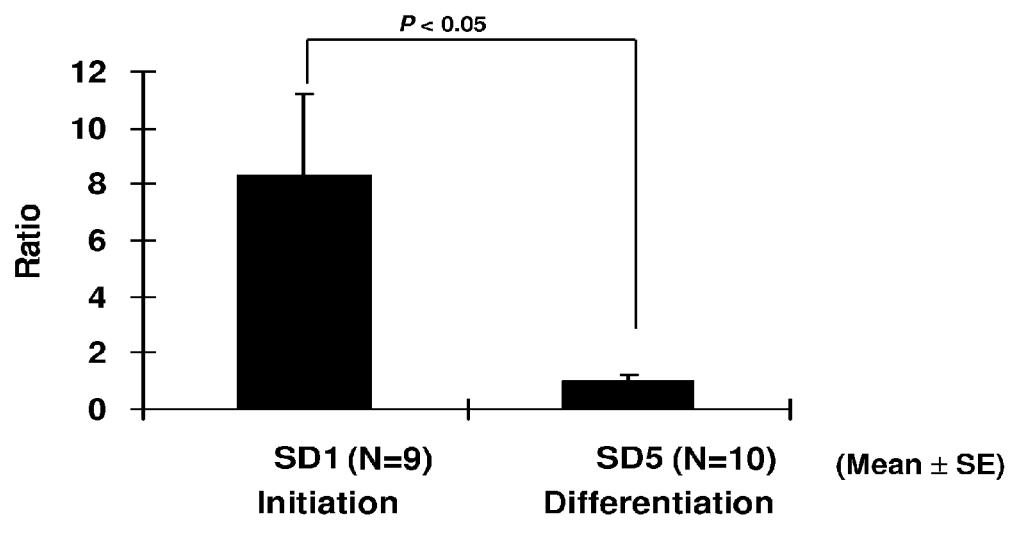
FIG. 1. FGF9 is expressed during inductive period of hair follicle regeneration at Day 1 after scab detachment (SD). The ratio of FGF9 mRNA compared to control mRNA expression q-PCR of FGF9 mRNA expression in regenerated epidermis is presented.

The invention relates to pharmaceutical compositions and methods for treating hair loss and regenerating hair follicles. Specifically, the invention relates to fibroblast growth factor-9 polypeptides and administering a fibroblast growth factor-9 polypeptide for treating hair loss or regenerating hair follicles.

The present invention provides methods of treating hair loss, treating, inhibiting, or suppressing a degenerative skin disorder, and treating androgenetic alopecia (AGA) in a subject and generating new hair follicles (HF) and increasing the size of existing HF, comprising epidermal disruption or administration of wnt, and administration of a fibroblast growth factor-9 polypeptide or another compound that upregulates sonic hedgehog gene signaling.

In one embodiment, the present invention provides methods of treating hair loss, methods for generating a hair follicle, methods for increasing the size of a hair follicle, methods for treating an androgenetic alopecia (AGA), methods for arresting alopecia, methods of reversing alopecia, and methods of depilation comprising administering a composition comprising a neutralizing fibroblast growth factor-9 antibody to a subject.

In another embodiment, a composition or method of the present invention is utilized on human skin. In another embodiment, the composition or method is utilized on an area of unwanted hair growth. In another embodiment, the area is the face. In another embodiment, the area is the bikini area. In another embodiment, the area is the legs. In another embodiment, the area is the arms. In another embodiment, the area is the chest.

In one embodiment, the methods of the present invention include contacting a subject with an inhibitor of FGF9, SHH, WNT, or other compositions for use in the present invention. An "inhibitor" utilized in methods and compositions of the present invention is, in another embodiment, an antibody that binds the protein or biological factor that is the target of the inhibitor. In another embodiment, the inhibitor is a pharmacologic inhibitor. In another embodiment, the inhibitor is any other type of inhibitor known in the art. Each possibility represents a separate embodiment of the present invention.

In one embodiment, the present invention provides a method of treating hair loss comprising the step of administering a composition comprising a fibroblast growth factor-9 polypeptide to a subject.

In one embodiment, the present invention provides a method of treating hair loss in a subject comprising the steps of (a) disrupting the epidermis in the region of said hair loss in said subject and (b) administering a composition comprising a fibroblast growth factor-9 polypeptide to said subject.

In another embodiment, the present invention provides a method of treating hair loss in a subject comprising the step administering a composition comprising a fibroblast growth factor-9 polypeptide and a wnt polypeptide to said subject.

In another embodiment, the present invention provides a method of treating hair loss in a subject comprising the steps of (a) disrupting the epidermis in the region of said hair loss in said subject and (b) administering a composition comprising a compound or factor that upregulates sonic hedgehog (SHH) to said subject.

In another embodiment, the present invention provides a method for treating an androgenetic alopecia (AGA) in a scalp of a subject comprising the steps of (a) disrupting the epidermis in the region of said AGA in said subject and (b) administering a composition comprising a fibroblast growth factor-9 polypeptide to said subject.

In another embodiment, the present invention provides a method for treating an to androgenetic alopecia (AGA) in a scalp of a subject comprising the step of administering a composition comprising a fibroblast growth factor-9 polypeptide and a wnt polypeptide to said subject.

In another embodiment, the present invention provides a method for treating an androgenetic alopecia (AGA) in a scalp of a subject comprising the steps of (a) disrupting the epidermis in the region of said hair loss in said subject and (b) administering a composition comprising a compound or factor that upregulates sonic hedgehog (SHH) to said subject.

In another embodiment, the present invention provides a method for generating a hair follicle in the dermis of a subject with hair loss comprising the steps of (a) disrupting the epidermis in the region of said hair loss in said subject and (b) administering a composition comprising a fibroblast growth factor-9 polypeptide to said subject.

In another embodiment, the present invention provides a method for generating a hair follicle in the dermis of a subject comprising the step of administering a composition comprising a fibroblast growth factor-9 polypeptide and a wnt polypeptide to said subject.

In another embodiment, the present invention provides a method for generating a hair follicle in the dermis of a subject comprising the steps of (a) disrupting the epidermis in the region of said hair loss in said subject and (b) administering a composition comprising a compound or factor that upregulates sonic hedgehog (SHH) to said subject.

In another embodiment, the present invention provides a method for increasing the size of a hair follicle in the dermis of a subject with hair loss comprising the steps of (a) disrupting the epidermis in the region of said hair loss in said subject and (b) administering a composition comprising a fibroblast growth factor-9 polypeptide to said subject.

In another embodiment, the present invention provides a method for increasing the size of a hair follicle in the dermis of a subject comprising the step of administering a composition comprising a fibroblast growth factor-9 polypeptide and a wnt polypeptide to said subject.

In another embodiment, the present invention provides a method for increasing the size of a hair follicle in the dermis of a subject comprising the steps of (a) disrupting the epidermis in the region of said hair loss in said subject and (b) administering a composition comprising a compound or factor that upregulates sonic hedgehog (SHH) to said subject.

In another embodiment, the present invention provides a method for increasing hair follicle formation in the skin of a subject with hair loss comprising the steps of (a) disrupting the epidermis in the region of said hair loss in said subject and (b) administering a composition comprising a fibroblast growth factor-9 polypeptide to said subject.

In another embodiment, the present invention provides a method for increasing hair follicle formation in the skin of a subject comprising the step of administering a composition comprising a fibroblast growth factor-9 polypeptide and a wnt polypeptide to said subject.

In another embodiment, the present invention provides a method for increasing hair follicle formation in the skin of a subject comprising the steps of (a) disrupting the epidermis in the region of said hair loss in said subject and (b) administering a composition comprising a compound or factor that upregulates sonic hedgehog (SHH) to said subject.

In another embodiment, the present invention provides a method for treating, inhibiting, or suppressing a degenerative skin disorder comprising the steps of (a) disrupting the epidermis in the region of said degenerative skin disorder in said subject and (b) administering a composition comprising a fibroblast growth factor-9 polypeptide to said subject.

In another embodiment, the present invention provides a method for treating, inhibiting, or suppressing a degenerative skin disorder comprising the step of administering a composition comprising a fibroblast growth factor-9 polypeptide and a wnt polypeptide to said subject.

In another embodiment, the present invention provides a method for treating, inhibiting, or suppressing a degenerative skin disorder comprising the steps of (a) disrupting the epidermis in the region of said hair loss in said subject and (b) administering a composition comprising a compound or factor that upregulates sonic hedgehog (SHH) to said subject.

In one embodiment, the methods of the present invention treat, inhibit or suppress a degenerative skin disorder. In one embodiment, a degenerative skin disorder is Hyperkeratosis, hyperpigmentation, depigmentation, atrophy, or a combination thereof. In one embodiment, a degenerative skin disorder is calcinosis; circumscripta; cutis; Colloid milium; skin degeneration; Senile dermatosis NOS; or Subcutaneous calcification.

In another embodiment, a degenerative skin disorder is granuloma annulare. In one embodiment, the degenerative skin disorder is localized granuloma annulare, which in one embodiment, is the most common form of granuloma annulare and in another embodiment, is characterized by the presence of small, firm red or yellow colored bumps (nodules or papules) that appear arranged in a ring on the skin. In one embodiment, the sizes of the lesions range from one to five centimeters. In one embodiment, the most commonly affected sites include the feet, hands, and fingers. In other embodiments, the degenerative skin disorder is generalized or disseminated, linear, perforating, or subcutaneous granuloma annulare. In one embodiment, the lesions associated with granuloma annulare may disappear without treatment (spontaneous remission) and reappear.

In another embodiment, the methods of the present invention are suitable for the prophylaxis and treatment of dryness, roughness of the skin, the formation of dry lines, reduced rehydration by sebaceous glands and an increased susceptibility to mechanical stress (tendency to crack), for the treatment of photodermatoses, the symptoms of senile xerosis, photoaging and other degenerative conditions which are associated with a decomposition of the connective tissue (collagen and elastin fibres and also glucosaminoglycans/hyaluronane) of the skin. "Photoaging" denotes the wrinkling, dryness and decreasing elasticity of the skin brought about by light and in particular UV radiation.

Further fields of application of the compositions according to the invention are the treatment and prevention of age- and/or UV-induced collagen degeneration and also the decomposition of elastin and glycosaminoglycans; of degenerative skin conditions such as loss of elasticity and also atrophy of the epidermal and dermal cell layers, of constituents of the connective tissue, of rete pegs and capillary vessels) and/or the skin adnexa; of environmentally-triggered negative changes in the skin and the skin adnexa, e.g. caused by ultraviolet radiation, smoking, smog, reactive oxygen species, free radicals and similar; of deficitary, sensitive or hypoactive skin conditions or deficitary, sensitive or hypoactive skin adnexa conditions; the reduction in skin thickness; of skin slackness and/or skin tiredness; of changes in the transepidermal water loss and normal moisture content of the skin; of a change in the energy metabolism of healthy skin; of deviations from the normal cell-cell communication in the skin which can manifest themselves e.g. in wrinkling; of changes in the normal fibroblast and keratinocyte proliferation; of changes in the normal fibroblast and keratinocyte differentiation; of polymorphic actinodermatosis, vitiligo; of wound healing disorders; disturbances to the normal collagen, hyaluronic acid, elastin and glycosaminoglycan homeostasis; of increased activation of proteolytic enzymes in the skin, such as e.g. metalloproteinases.

In another embodiment, the present invention provides a method of treating hair loss, generating a hair follicle, increasing the size of a hair follicle, increasing hair follicle formation, treating, inhibiting or suppressing a degenerative skin disorder, treating androgenetic alopecia (AGA), comprising any combination of the following steps: (a) disrupting the epidermis in the region of said hair loss in said subject; (b) administering a fibroblast growth factor-9 polypeptide; (c) administering a wnt polypeptide; and (d) administering a compound or factor that upregulates Sonic Hedgehog (SHH), Patched-1 (Ptch1), Patched-2 (Ptch2), Gli1, Gli2, or a combination thereof to said subject.

In another embodiment, the present invention provides a method of depilation comprising the step of administering a composition comprising a neutralizing fibroblast growth factor-9 antibody to a subject. In one embodiment, the antibody is administered at a concentration of 10 µg/mL. In one embodiment, the depilation is in the legs, arms, underarms, pubic area, back, face, nose, or ears of said subject. In one embodiment, the method further comprises the step of disrupting the epidermis in the region of said depilation prior to said administering step. In one embodiment, the step of contacting is performed 3-12 days after said step of disrupting. In one embodiment, the step of disrupting is performed by exposing the region of said hair loss to a mechanical, chemical, or optical stimulus. In one embodiment, the optical stimulus is radiation. In one embodiment, the administering step is via topical administration. In another embodiment, the administering step is via subcutaneous administration.

In another embodiment, the present invention provides a method of reversing alopecia comprising the step of administering a composition comprising a fibroblast growth factor-9 polypeptide to a bald or balding subject. In another embodiment, the present invention provides a method of arresting alopecia comprising the step of administering a composition comprising a fibroblast growth factor-9 polypeptide to a bald or balding subject.

In another embodiment, the present invention provides a method of treating a wound in a subject comprising the step of administering a composition comprising a fibroblast growth factor-9 polypeptide to a bald or balding subject. In another embodiment, the present invention provides a method of treating an injury in a subject comprising the step of administering a composition comprising a fibroblast growth factor-9 polypeptide to a bald or balding subject.

FGF9

In one embodiment, the methods of the present invention comprise the step of administering a composition comprising a fibroblast growth factor-9 polypeptide, alone or in composition with one or more additional compounds. In one embodiment, FGF9 refers to Fgf-9, FGF-9, Fibroblast growth factor 9, GAF, glia activating factor, Glia-activating factor precursor, or HBGF-9. In one embodiment, the FGF9 protein of the methods of the present invention has the sequence: IFPNGTIQGTRKDHSRFGILEFISIA-VGLVSIRGVDSGLYLGMNEKGELYGSEKLTQECV FREQFEENWYNTYSSNLYKHVDTGRRYY-VALNKDGTPREGTRTKRHQKFTHFLPRP VDPDKVPE-LYKDILSQS (GenBank Accession No: BAA03572; SEQ ID No: 1). In another embodiment, the FGF9 protein has a sequence as set forth in GenBank Accession No. P31371, BAF83481, NP_002001, CAC17692, EAX08316, AAI03980, AAI03979, AAT74624 or AAH69692. In another embodiment, the FGF9 protein is encoded by a genomic nucleic acid molecule having a sequence as set forth in GenBank Accession No. AL139378.15, AY682094.1, or CH471075.1 or encoded by an mRNA molecule having a sequence as set forth in GenBank Accession No. AK290792.1, BC069692.1, BC103978.1, BC103979.1, CR746503.1, or D14838.1. In another embodiment, a biologically active fragment of an FGF9 protein is utilized in a method of the present invention. In another embodiment, a homolog of an FGF9 protein is utilized in a method of the present invention. Each possibility represents a separate embodiment of the present invention.

Figure 14:
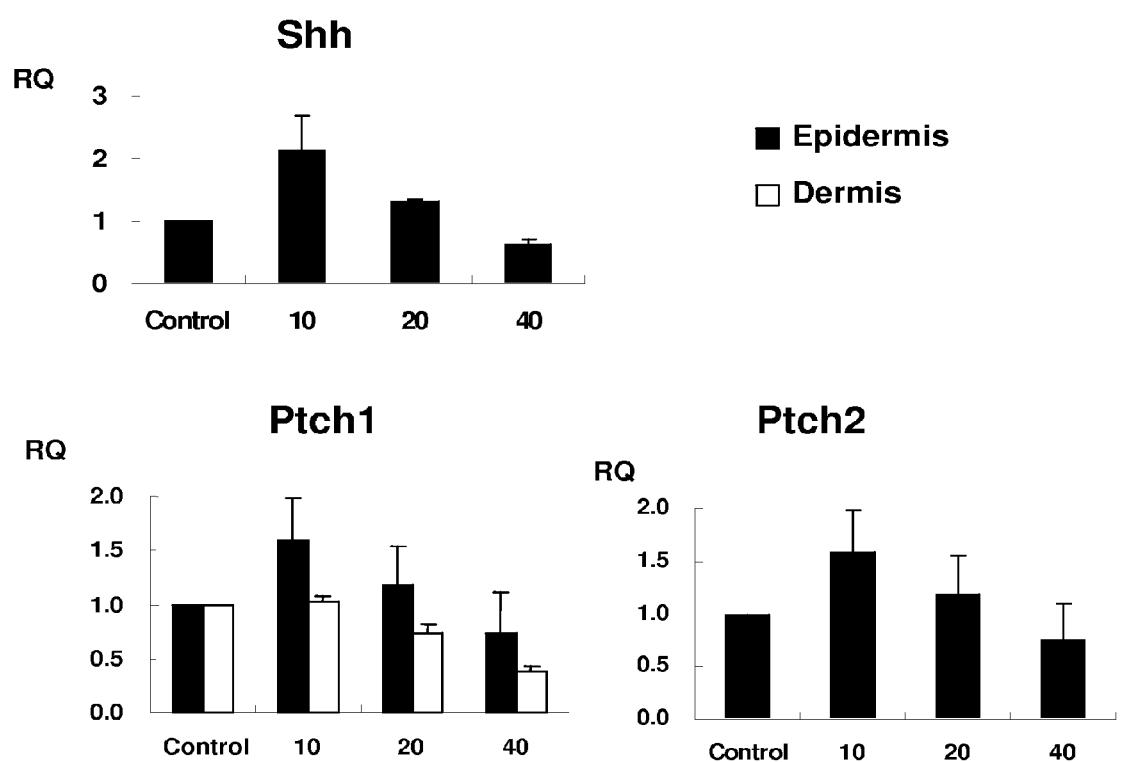
FIG. 14. Effect of 24 h treatment using rhFGF9 (10, 20, 40 ng/ml) on markers of embryonic hair follicle development sonic hedgehog (Shh), Ptch1, and Ptch2 by qPCR.

In one embodiment, administration of recombinant human FGF9 increased levels of sonic hedgehog (SHH) gene expression (FIG. 14).

Shh

In one embodiment, the methods of the present invention comprise the step of administering a composition comprising a sonic hedgehog (SHH) polypeptide, alone or in composition with one or more additional compounds. In another embodiment, the methods of the present invention comprise the step of administering a compound or factor that increases SHH expression. In one embodiment, SHH refers to TPT; HHG1; HLP3; HPE3; SMMCI; TPTPS; or MCOPCB5. In one embodiment, the SHH protein of the methods of the present invention has the sequence:
MLLLARCLLLVLVSSLLVCSGLACG-PGRGFGKRRHPKKLTPLAYKQFIPNVAEK TLGAS-GRYEGKISRNSERFKELTPNYNPDI-IFKDEENTGADRLMTQRCKDKLNALAISV MNQWPGVKLRVTEGWDEDGHHSEESL-HYEGRAVDITTSDRDRSKYGMLARLAVEAG FDWVYYESKAHIHCSVKAENSVAAKSG-GCFPGSATVHLEQGGTKLVKDLSPGDRVLA ADDQGRLLYSDFLTFLDRDDGAKKV-FYVIETREPRERLLLTAAHLLFVAPHNDSATGEP EAS-SGSGPPSGGALGPRALFASRVR-PGQRVYVVAERDGDRRLLPAAVHSVTLSEEAAG AYAPLTAQGTILINRVLASCYAVIEEH-SWAHRAFAPFRLAHALLAALAPARTDRGGDS GGGDRGGGGGRVALTAPGAADAP-GAGATAGIHWYSQLLYQIGTWLLDSEALHPLGM AVKSS (GenBank Accession No: Q15465.1; SEQ ID No: 2). In another embodiment, the SHH protein has a sequence as set forth in GenBank Accession No. BAA34689.1; AAB67604.1; AAS01990.1; AAQ87879.1; EAL23913.1; EAX04543.1; AAA62179.1; or AAI11926.1. In another embodiment, the SHH protein is encoded by a nucleic acid having a sequence as set forth in GenBank Accession No. AB020410.1; AC002484.1; AC078834.5; AY422195.1; CH236954.1; CH471149.1; AY927450.1; L38518.1; or BC111925.1. In another embodiment, a biologically active fragment of a SHH protein is utilized in a method of the present invention. In another embodiment, a homolog of a SHH protein is utilized in a method of the present invention. Each possibility represents a separate embodiment of the present invention.

In one embodiment, SHH binds to the patched (PTC) receptor, which functions in association with smoothened (SMO), to activate the transcription of target genes. In the absence of SHH, PTC represses the constitutive signaling activity of SMO. In another embodiment, SHH also regulates the gli oncogene. In another embodiment, SHH is an intercellular signal essential for a variety of patterning events during development: signal produced by the notochord that induces ventral cell fate in the neural tube and somites, and the polarizing signal for patterning of the anterior-posterior axis of the developing limb bud. In another embodiment, SHH displays to both floor plate- and motor neuron-inducing activity.

In another embodiment, administration of recombinant human FGF9 increased levels of Patched homolog 1 (Drosophila), (PTCH1; FIG. 14), which in one embodiment, is a human gene. In one embodiment, Ptch1 encodes a member of the patched gene family. In one embodiment, Ptch1 is the receptor for sonic hedgehog (SHH), which in one embodiment, is a secreted molecule implicated in the formation of embryonic structures and in tumorigenesis. In one embodiment, Ptch1 functions as a tumor suppressor. In one embodiment, mutations of Ptch1 have been associated with nevoid basal cell carcinoma syndrome, esophageal squamous cell carcinoma, trichoepitheliomas, transitional cell carcinomas of the bladder, as well as holoprosencephaly. In one embodiment, alternative splicing of Ptch1 results in multiple transcript variants encoding different isoforms.

PTCH1

In one embodiment, the methods of the present invention comprise the step of administering a composition comprising a Patched-1 (PTCH1) polypeptide, alone or in composition with one or more additional compounds. In another embodiment, the methods of the present invention comprise the step of administering a compound or factor that increases PTCH1 expression. In one embodiment, PTCH1 refers to PTC; BCNS; HPE7; PTC1; PTCH; NBCCS; PTCH11; FLJ26746; or FLJ42602. In one embodiment, the PTCH1 protein of the methods of the present invention has the sequence:
MASAGNAAEPQDRGGGGS-GCIGAPGRPAGGGRRRRTGGLRRAAAPDRDYLHR PSYCDAAFALEQISKGKATGRKAPLWL-RAKFQRLLFKLGCYIQKNCGKFLVVGLLIFGA FAVGLKAANLETNVEELWVEVGGRVS-RELNYTRQKIGEEAMFNPQLMIQTPKEEGAN VLT-TEALLQHLDSALQASRVHVYMYN-RQWKLEHLCYKSGELITETGYMDQIIEYLYPC LIITPLDCFWEGAKLQSGTAYLLGKPPL-RWTNFDPLEFLEELKKINYQVDSWEEMLNKA EVGH-GYMDRPCLNPADPDCPATAPNKNSTK-PLDMALVLNGGCHGLSRKYMHWQEEL IVGGTVKNSTGKLVSAHALQTMFQLMTP-KQMYEHFKGYEYVSHINWNEDKAAAILEA WQR-TYVEVVHQSVAQNSTQKVLSFTTTTLD-DILKSFSDVSVIRVASGYLLMLAYACLT MLRWDCSKSQGAVGLAGVLLVALSVAA-GLGLCSLIGISFNAATTQVLPFLALGVGVDD VFLLA-HAFSETGQNKRIPEDRTGECLKRTGAS-VALTSISNVTAFFMAALIPIPALRAFSL QAAVVVVFNFAMVLLIFPAILSMDLYRREDRRLDIFCCFTSPCVSRVIQVEPQAYTDTHDNTRYSPPPPYSSHSFAHETQITMQSTVQLRTEYDPHTHVYYTTAEPRSEISVQPVTVTQDTLSCQSPESTSSTRDLLSQFSDSSLHCLEPPCTKWTLSSFAEKHYAPFLLKPKAKVVVIFLFLGLLGVSLYGTTRVRDGLDLTDIVPRETREYDFIAAQFKYFSFYNMYIVTQKADYPNIQHLLYDLHRSFSNVKYVMLEENKQLPKMWLHYFRDWLQGLQDAFDSDWETGKIMPN NYKNGSDDGVLAYKLLVQTGSRDKPIDISQLTKQRLVDADGIINPSAFYIYLTAWVSNDPVAYAASQANIRPHRPEWVHDKADYMPETRLRIPAAEPIEYAQFPFYLNGLRDTSDFVEAIEKVRTICSNYTSLGLSSYPNGYPFLFWEQYIGLRHWLLLFISVVLACTFLVCAVFLLNPWTAGIIVMVLALMTVELFGMMGLIGIKLSAVPVVILIASVGIGVEFTVHVALAFLTAIGD KNRRAVLALEHMFAPVLDGAVSTLLGVLMLAGSEFDFIVRYFFAVLAILTILGVLNGLVLLPVLLSFFGPYPEVSPANGLNRLPTPSPEPPPSVVRFAMPPGHTHSGSDSSDSEYSSQTTVSGLSEELRHYEAQQGAGGPAHQVIVEATENPVFAHSTVVHPESRHHPPSNPRQQPHLDSGSLPPGRQGQQPRRDPPREGLWPPPYRPRRDAFEISTEGHSGPSNRARWGPRGARSHNPRNPASTAMGSSVPGYCQPITTVTASASVTVAVHPPPVPGPGRNPRGGLCPGYPETDHGLFEDPHVPFHVRCERRDSKVEVIELQDVECEERPRGSSSN (GenBank Accession No: Q13635.2; SEQ ID No: 3). In another embodiment, the PTCH1 protein has a sequence as set forth in GenBank Accession No. CAH73817.1; CAH73818.1; CAH73819.1; AAR21238.1; AAR21239.1; AAR21240.1; EAW92631.1; EAW92632.1; BAD74184.1; BAD74185.1; BAD74186.1; BAD74187.1; BAD74188.1; BAD92732.1; BAF47711.1; BAE45300.1; BAE45302.1; BAE45304.1; BAF47712.1; BAC85893.1; AAH43542.1; AAC50496.1; AAC50550.1; or AAI52920.1. In another embodiment, the PTCH1 protein is encoded by a nucleic acid having a sequence as set forth in GenBank Accession No. AL161729.27; AY395758.1; AY395768.1; AY395772.1; CH471174.1; AB189436.1; AB189437.1; AB189438.1; AB189439.1; AB189440.1; AB209495.1; AB212827.1; AB212828.1; AB214500.1; AB233422.1; AB233424.1; AB239329.1; AI358880.1; AI494442.1; AK124593.1; AK130256.1; BC043542.1; BF195352.1; BM974119.1; BX117041.1; CR744004.1; DB093644.1; U43148.1; U59464.1; or BC152919.1. In another embodiment, a biologically active fragment of an PTCH1 protein is utilized in a method of the present invention. In another embodiment, a homolog of an PTCH1 protein is utilized in a method of the present invention. Each possibility represents a separate embodiment of the present invention.

In another embodiment, administration of recombinant human FGF9 increased levels of Patched homolog 2 (Drosophila), (PTCH; FIG. 14)

PTCH2

In one embodiment, the methods of the present invention comprise the step of administering a composition comprising a Patched-2 (PTCH2) polypeptide, alone or in composition with one or more additional compounds. In another embodiment, the methods of the present invention comprise the step of administering a compound or factor that increases PTCH2 expression. In one embodiment, ptch2 encodes a member of the patched gene family. In one embodiment, the patched protein is the receptor for sonic hedgehog, a secreted molecule implicated in the formation of embryonic structures and in tumorigenesis. In one embodiment, ptch2 is mutated in a medulloblastoma and in a basal cell carcinoma, suggesting that it plays a role in the development of some tumors. Alternative transcript variants have been described, but their biological function has not been determined. In one embodiment, the PTCH2 polypeptide for use in the methods of the present invention has the sequence:

FDFIVRYFFAALTVLTLLGLLHGLVLLPVLLSILGPPPEVIQMYKESPEILSPPAPQ GGGLRVGSLQVNISYWKELLWCQDLRPEEI (GenBank Accession No: □5JR97; SEQ ID to No: 4). In another embodiment, the PTCH2 protein has a sequence as set forth in GenBank Accession No. CAI23127.1; CAI13000.1; AAR05447.1; EAX07017.1; AAD25953.1; AAC79847.1; AAD17260.1; AAQ88919.1; AAQ89375.1; or AAI52912.1. In another embodiment, the PTCH2 protein is encoded by a nucleic acid having a sequence as set forth in GenBank Accession No. AL136380.22; AL592166.16; AY438664.1; CH471059.2; AF087651.1; AF091501.1; AF119569.1; AK307168.1; AY358555.1; AY359016.1; or BC152911.1. In another embodiment, a biologically active fragment of a PTCH2 protein is utilized in a method of the present invention. In another embodiment, a homolog of a PTCH2 protein is utilized in a method of the present invention. Each possibility represents a separate embodiment of the present invention.

GLI1

In one embodiment, the methods of the present invention comprise the step of administering a composition comprising a glioma-associated oncogene homolog 1 (zinc finger protein) (GLI1) polypeptide, alone or in a composition with one or more additional compounds. In one embodiment, gli1 encodes a protein which is a member of the Kruppel family of zinc finger proteins. In another embodiment, the methods of the present invention comprise the step of administering a compound or factor that increases GLI1 expression. In one embodiment, the GLI1 polypeptide for use in the methods of the present invention has the sequence:

MFNSMTPPPISSYGEPCCLRPLPSQGAPSVGTEGLSGPPFCHQANLMSGPHSYGP ARETNSCTEGPLFSSPRSAVKLTKKRALSISPLSDASLDLQTVIRTSPSSLVAFINSRCTSPGGSYGHLSIGTMSPSLGFPAQMNHQKGPSPSFGVQPCGPHDSARGGMIPHPQSRGPFPTCQLKSELDMLVGKCREEPLEGDMSSPNSTGIQDPLLGMLDGREDLEREEKREPESVYET DCRWDGCSQEFDSQEQLVHHINSEHIHGERKEFVCHWGGCSRELRPFKAQYMLVVHMRRHTGEKPHKCTFEGCRKSYSRLENLKTHLRSHTGEKPYMCEHEGCSKAFSNASDRAK HQNRTHSNEKPYVCKLPGCTKRYTDPSSLRKHVKTVHGPDAHVTKRHRGDGPLPRAPSISTVEPKREREGGPIREESRLTVPEGAMKPQPSPGAQSSCSSDHSPAGSAANTDSGVEMTGNAGGSTEDLSSLDEGPCIAGTGLSTLRRLENLRLDQLHQLRPIGTRGLKLPSLSHTGT TVSRRVGPPVSLERRSSSSSSISSAYTVSRRSSLASPFPPGSPPENGASSLPGLMPAQHYLLRARYASARGGGTSPTAASSLDRIGGLPMPPWRSRAEYPGYNPNAGVTRRASDPAQA ADRPAPARVQRFKSLGCVHTPPTVAGGGQNFDPYLPTSVYSPQPPSITENAAMDARGLQEEPEVGTSMVGSGLNPYMDFPPTDTLGYGGPEGAAAEPYGARGPGSLPLGPGPPTNYGPNPCPQQASYPDPTQETWGEFPSHSGLYPGPKALGGTYSQCPRLEHYGQVQVKPEQGCPVGSDSTGLAPCLNAHPSEGPPHPQPLFSHYPQPSPPQYLQSGPYTQPPPDYLPSEPRP CLD

FDSPTHSTGQLKAQLVCNYVQSQQELLWEGGGREDAPAQEPSYQSPKFLGGSQVSPSRAKAPVNTYGPGFGPNLPNHKSGSYPTPSPCHENFVVGANRASHRAAAPPRLLPPLPTCYGPLKVGGTNPSCGHPEVGRLGGGPALYPPPEGQVCNPLDSLDLDNTQLDFVAILD EPQGLSPPPSHDQRGSSGHTPPPSGPPNMAVGNMSVLLRSLPGETEFLNSSA (GenBank Accession No: P08151; SEQ ID No: 5). In another embodiment, the GLI1 protein has a sequence as set forth in GenBank Accession No. AAM13391.1; EAW97013.1; BAG60219.1; AAH13000.1; or CAA30297.1. In another embodiment, the GLI1 protein is encoded by a nucleic acid having a sequence as set forth in GenBank Accession No. AC022506.38; AF316573.1; CH471054.1; AK297899.1; BC013000.2; or X07384.1. In another embodiment, a biologically active fragment of a GLI1 protein is utilized in a method of the present invention. In another embodiment, a homolog of a GLI1 protein is utilized in a method of the present invention. Each possibility represents a separate embodiment of the present invention.

GLI2

In one embodiment, the methods of the present invention comprise the step of administering a composition comprising a glioma-associated oncogene homolog 2 (zinc finger protein) (GLI2) polypeptide, alone or in a composition with one or more additional compounds. In another embodiment, the methods of the present invention comprise the step of administering a compound or factor that increases GLI2 expression. In one embodiment, GLI2 may be referred to as HPE9; THP1; or THP2. In one embodiment, gli2 encodes a protein which belongs to the C2H2-type zinc finger protein subclass of the Gli family. Members of this subclass are characterized as transcription factors which bind DNA through zinc finger motifs. These motifs contain conserved H—C links. Gli family zinc finger proteins are mediators of Sonic hedgehog (Shh) signaling and they are implicated as potent oncogenes in the embryonal carcinoma cell. The protein encoded by this gene localizes to the cytoplasm and activates patched *Drosophila* homolog (PTCH) gene expression. It is also thought to play a role during embryogenesis. The encoded protein is associated with several phenotypes-Greig cephalopolysyndactyl)-syndrome, Pallister-Hall syndrome, preaxial polydactyly type IV, postaxial polydactyly types A1 and B. In one embodiment, the GLI2 polypeptide for use in the methods of the present invention has the sequence: MALTSINATPTQLSSSSNCLSDTNQNKQSSESAVSSTVNPVAIHKRSKVKTEPEGLRPAS PLALTQGQVLDTAHVGVPFPSPQEQLADLKEDLDRDDCKQEAEVVIYETNCHWEDCT KEYDTQEQLVHHINNEHIHGEKKEFVCRWQACTREQKPFKAQYMLVVHMRRHTGEK PHKCTFEGCSKAYSRLENLKTHLRSHTGEKPYVCEHEGCNKAFSNASDRAKHQNRTHSNEKPYICKIPGCTKRYTDPSSLRKHVKTVHGPDAHVTKKQRNDVHLRTPLLKENGDSEAGTEPGGPESTEASSTSQAVEDCLHVRAIKTESSGLCQSSPGAQSSCSSEPSPLGSAPNNDSGVEMPGTGPGSLGDLTALDDTPPGADTSALAAPSAGGLQLRKHMTTMHRFEQLKKEKLKSLKDSCSWAGPTPHTRNTKLPPLPGSGSILENFSGSGGGPAGLLPNPRLSELSAS EVTMLSQLQERRDSSTSTVSSAYTVSRRSSGISPYFSSRRSSEASPLGAGRPHNASSADSYDPISTDASRRSSEASQCSGGSGLLNLTPAQQYSLRAKYAAATGGPPPTPLPGLERMSL RTRLALLDAAEGTLPAGCPRPLGPRRGSDGPTYGHGHAGAAPAFPHEAPGGGTRRASDPVRRPDALSLPRVQRFHSTHNVNPGPLPPCADRRGLRLQSHPSTDGGLARGAYSPRPPSI SENVAMEAVAAGVDGAGPEADLGLPEDDLVLPDDVVQYIKAHASGALDEGTGQVYPTESTGFSDNPRLPSPGLHGQRRMVAADSNVGPSAPMLGGCQLGFGAPSSLNKNNMPVQWNEVSSGTVDSLASQVKPPPFPQGNLAVVQQKPAFGQYPGYSPQGLQASPGGLDSTQPHLQPRSGAPSQGIPRVNYMQQLRQPVAGSQCPGMTTTMSPHACYGQVHPQLSPSTISGALNQFPQSCSNMPAKPGHLGHPQQTEVAPDPTTMGNRHRELGVPNSALAGVPPPHPVQSYPQQSHHLAASMSQEGYHQVPSLLPARQPGFMEPQTGPMGVATAGFGLVQPRPP LEPSPTGRHRGVRAVQQQLAYARATGHAMAAMPSSQETAEAVPKGAMGNMGSVPPQPPPQDAGGAPDHSMLYYYGQIMYEQDGGLENLGSCQVMRSQPPQPQACQDSIQPQP LPSPGVNQVSSTVDSQLLEAPQIDFDAIMDDGDHSSLFSGALSPSLLHSLSQNSSRLTTPRNSLTLPSIPAGISNMAVGDMSSMLTSLAEESKFLNMMT (GenBank Accession No: P10070; SEQ ID No: 6). In another embodiment, the GLI2 protein has a sequence as set forth in GenBank Accession No. AAA35898.1; BAA25665.1; BAA25666.1; BAA25667.1; BAA25668.1; BAD92591.1; BAG61875.1; AAS72889.1; AAS72890.1; AAS72891.1; AAI11411.1; BAA03568.1; BAA03569.1; AAY58315.1; AAY58316.1; AAY58317.1; or AAY87165.1. In another embodiment, the GLI2 protein is encoded by a nucleic acid having a sequence as set forth in GenBank Accession No. AC016764.8; AC017033.5 (60664.181887); M20672.1; M20673.1; AB007295.1; AB007296.1; AB007297.1; AB007298.1; AB209354.1; AJ707583.1; AK300071.1; AY493737.1; AY493738.1; AY493739.1; BC111410.1; D14827.1; D14828.1; DQ004396.1; DQ004397.1; DQ004398.1; or DQ086814.1. In another embodiment, a biologically active fragment of a GLI2 protein is utilized in a method of the present invention. In another embodiment, a homolog of a GLI2 protein is utilized in a method of the present invention. Each possibility represents a separate embodiment of the present invention.

WNT

In one embodiment, the methods of the present invention comprise the step of administering a composition comprising a Wnt polypeptide. The Wnt polypeptide of methods and compositions of the present invention is, in another embodiment, the sequence: MNRKARRCLGHLFLSLGMVYLRIGGFSSVVALGASIICNKIPGLAPRQRAICQSRPDAII VIGEGSQMGLDECQFQFRNGRWNCSALGERTVFGKELKVGSREAAFTYAIIAAGVAH AITAACTQGNLSDCGCDKEKQGQYHRDEGWKWGGCSADIRYGIGFAKVFVDAREIK QNARTLMNLHNNEAGRKILEENMKLECKCHGVSGSCTTKTCWTTLPQFRELGYVLK DKYNEAVHVEPVRASRNKRPTFLKIKKPLSYRKPMDTDLVYIEKSPNYCEEDPVTGS VGTQGRACNKTAPQASGCDLMCCGRGYNTHQYARVWQCNCKFHWCCYVKCNTCS ERTEMYTCK (GenBank Accession No: BC008811; SEQ ID No: 7). In another embodiment, the Wnt polypeptide has a sequence selected from the sequences set forth in GenBank entries NM_004625, D83175, U53476, and NP_004616. In another embodiment, the Wnt polypeptide is a Wnt7 protein. In another embodiment, the Wnt polypeptide is a Wnt7a polypeptide. In another embodiment, the Wnt polypeptide is Wnt1 protein. In another embodiment, the Wnt polypeptide is a Wnt3 polypeptide. In another embodiment, the Wnt polypeptide is a Wnt3a polypeptide. In another embodiment, the Wnt polypeptide is a Wnt10 polypeptide. In another embodiment, the Wnt polypeptide is a Wnt10a protein. In another embodiment, the Wnt polypeptide is a Wnt10b polypeptide. In another embodiment, the Wnt polypeptide is encoded by a nucleic acid molecule having a sequence set forth in the one of the above GenBank entries. In another embodiment, a biologically active fragment of a Wnt polypeptide is utilized in a method of the present invention. In another embodiment, a biologically active fragment of a Wnt7 protein is utilized in a method of the present invention. In another embodiment, a biologically active fragment of a Wnt polypeptide is utilized in a method of the present invention. In another embodiment, a biologically active fragment of a Wnt7a polypeptide is utilized in a method of the present invention. Each possibility represents a separate embodiment of the present invention.

In another embodiment, methods of the present invention stimulate one or more members of the SHH signaling pathway, which in one embodiment is N-Shh (cleavage product), N-Shh-Chol, which in one embodiment, inhibits Patched-1 and Patched-2, which in one embodiment, inhibit Smoothened, which in one embodiment, stimulates GLI-1, which in one embodiment, stimulates transcription of other genes (in one embodiment, GLI-1, PTC1, HNF3(3) and GLI-2, and GLI-3, which in one embodiment inhibit transcription of other genes. Thus, in one embodiment, FGF9 stimulation and the resulting increase in SHH will relieve the tonic inhibition of Patched proteins on the Smoothened protein and increase levels of GLI-1, leading to enhancement of gene transcription.

In another embodiment, methods of the present invention stimulate one or more members of the WNT signaling pathway, which in one embodiment is Frizzled, SFRP, Dishevelled (Dsh), TCF, LRP, APC, β-catenin, Axin, Dickkopf, GSK3, Naked, Porcupine, or FRAT/GBP.

In another embodiment, the wnt pathway is stimulated before the hedgehog pathway. In another embodiment, the two pathways are stimulated in an overlapping fashion. In another embodiment, the two pathways are stimulated simultaneously. Each possibility represents a separate embodiment of the present invention.

In another embodiment, homologues and variants of transcripts and proteins of the present invention are administered in methods of the present invention. In another embodiment, homologues and variants of transcripts and proteins of the present invention are targeted in methods of the present invention. Each possibility represents a separate embodiment of the present invention.

The terms "homology," "homologous," etc, when in reference to any protein or peptide, refer in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

In another embodiment, the term "homology," when in reference to any nucleic acid sequence similarly indicates a percentage of nucleotides in a candidate sequence that are identical with the nucleotides of a corresponding native nucleic acid sequence.

In another embodiment, "homology" refers to identity of greater than 70%. In another embodiment, "homology" refers to identity of greater than 75%. In another embodiment, "homology" refers to identity of greater than 80%. In another embodiment, "homology" refers to identity of greater than 82%. In another embodiment, "homology" refers to identity of greater than 85%. In another embodiment, "homology" refers to identity of greater than 87%. In another embodiment, "homology" refers to identity of greater than 90%. In another embodiment, "homology" refers to identity of greater than 92%. In another embodiment, "homology" refers to identity of greater than 95%. In another embodiment, "homology" refers to identity of greater than 97%. In another embodiment, "homology" refers to identity of greater than 98%. In another embodiment, "homology" refers to identity of greater than 99%. In another embodiment, "homology" refers to identity of 100%.

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the present invention.

In one embodiment, the term "peptide" includes native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into bacterial cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein.

Peptide bonds (—CO—NH—) within the peptide may be substituted, for example, by N-methylated bonds (—N (CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH (OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

In another embodiment, naturally occurring amino acids and non-conventional or modified amino acids as are known in the art can be used with the present invention.

In another embodiment, the present invention provides a kit, comprising a tools and/or a compound suitable for performing a method of the present invention.

In another embodiment, the present invention provides a device, comprising a tool suitable for epidermal disruption and a means of delivering a compound or factor that upregulates expression of SHH.

It is to be understood that included in the present invention are methods comprising the step of administering an isolated nucleic acid, in one embodiment, a vector or plasmid, encoding a polypeptide of the present invention, which in one embodiment, is a fibroblast growth factor-9 polypeptide, shh, wnt, ptch1, ptch, gli1, or gli2, or a composition comprising such a vector.

In one embodiment, an isolated nucleic acid that encodes a polypeptide of the present invention for use in the methods of the present invention is provided.

In one embodiment, an "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid to gene encoding additional polypeptide sequence.

In one embodiment, the present invention provides a cell comprising an isolated nucleic acid or vector of the present invention.

In one embodiment, two polynucleotides of the present invention are operably linked. For example, in one embodiment, polynucleotides encoding FGF9 and WNT may be operably linked. In one embodiment, "operably linked" indicates that a single-stranded or double-stranded nucleic acid moiety comprises the two polynucleotides arranged within the nucleic acid moiety in such a manner that they are expressed together. By way of example, a promoter operably linked to the coding region of a gene is able to promote transcription of the coding region.

In one embodiment, a polynucleotide of the present invention comprises a promoter/regulatory sequence, which in one embodiment, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

In one embodiment, the term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner. In one embodiment, a promoter used in the present invention may be constitutive or inducible. In another embodiment, a promoter for use in the methods of the present invention may be tissue-specific. Such promoters are well known in the art.

In another embodiment, the present invention provides a delivery vehicle for administration of a polypeptide of the present invention. Examples of such delivery vehicles are to known in the art and may include recombinant viruses or bacteria engineered to express said polypeptide. In one embodiment, said viruses or bacteria are attenuated. In one embodiment, viruses for use in the methods of the present invention may include retroviruses, adenoviruses, adeno-associated viruses, etc. In one embodiment, the virus may be of any known serotype or subgroup.

In one embodiment, any one of a number of different vectors can be used in the methods of the present invention, such as viral vectors, plasmid vectors, linear DNA, etc., as known in the art, to introduce an exogenous nucleic acid fragment encoding a therapeutic agent into target cells and/or tissue. These vectors can be inserted, for example, using infection, transduction, transfection, calcium-phosphate mediated transfection, DEAE-dextran mediated transfection, electroporation, liposome-mediated transfection, biolistic gene delivery, liposomal gene delivery using fusogenic and anionic liposomes (which are an alternative to the use of cationic liposomes), direct injection, receptor-mediated uptake, magnetoporation, ultrasound, or any combination thereof, as well as other techniques known in the art (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals). The polynucleotide segments encoding sequences of interest can be ligated into an expression vector system suitable for transducing mammalian cells and for directing the expression of recombinant products within the transduced cells. The introduction of the exogenous nucleic acid fragment is accomplished by introducing the vector into the vicinity of the micro-organ. Once the exogenous nucleic acid fragment has been incorporated into the cells using any of the techniques described above or known in the art, the production and/or the secretion rate of the therapeutic agent encoded by the nucleic acid fragment can be quantified. In one embodiment, the term "exogenous" refers to a substance that originated outside, for example a nucleic acid that originated outside of a cell or tissue.

In one embodiment, a vector for use in the methods of the present invention is a non-immunogenic gene transfer agent such as a nonviral vector (e.g. DNA plasmids or minicircle DNA), a "gutless" viral vector i.e. without endogenous genes (which in one embodiment, is due to a deletion, while in another embodiment, due to an insertion, substitution or deletion in a gene that prevents gene expression), a helper-dependent adenovirus (HDAd) vector, or adeno associated virus AAV (which in one embodiment is single stranded and in another embodiment, double stranded). In another embodiment, said formulation is so chosen such that recombinant gene expression results in lack of toxicity or immune-mediated rejection of the gene product by the tissue. In one embodiment, the vector is virally derived, and in another embodiment, the vector is a plasmid. In one embodiment, the virally-derived vector is derived from adenovirus, which in one embodiment, is helper-dependent adenovirus, while in another embodiment, the virally-derived vector is derived from adenovirus-associated vector.

In one embodiment, the term "vector" or "expression vector" refers to a carrier molecule into which a nucleic acid sequence can be inserted for introduction into a cell where it can be replicated. In one embodiment, the nucleic acid molecules are transcribed into RNA, which in some cases are then translated into a protein, polypeptide, or peptide. In other cases, RNA sequences are not translated, for example, in the production of antisense molecules or ribozymes. In one embodiment, expression vectors can contain a variety of "control sequences" which refer to nucleic acid sequences necessary for the transcription and possibly translation of an operably linked coding sequence in a particular host cell. In another embodiment, a vector further includes an origin of replication. In one embodiment the vector may be a shuttle vector, which in one embodiment can propagate both in prokaryotic and eukaryotic cells, or in another embodiment, the vector may be constructed to facilitate its integration within the genome of an organism of choice. The vector, in other embodiments may be, for example, a plasmid, a bacmid, a phagemid, a cosmid, a phage, a virus or an artificial chromosome. In one embodiment, the vector is a viral vector, which in one embodiment may be a bacteriophage, mammalian virus, or plant virus.

In other embodiments, the viral vector is derived from a virus such as vaccinia virus, lentivirus, polio virus, hepatitis virus, papilloma virus, cytomegalovirus, simian virus, or herpes simplex virus.

In certain embodiments of the invention, the vector comprising a nucleic acid sequence may comprise naked recombinant DNA or plasmids. Transfer of the construct may be performed by any method which physically or chemically permeabilizes the cell membrane. In one embodiment, the vector is a mini-circle DNA, which in one embodiment, is a supercoiled DNA molecule for non-viral gene transfer, which has neither a bacterial origin of replication nor an antibiotic resistance marker.

Construction of vectors using standard recombinant techniques is well known in the art (see, for example, Maniatis, et al., Molecular Cloning, A Laboratory Manual (Cold Spring Harbor, 1990) and Ausubel, et al., 1994, Current Protocols in Molecular Biology (John Wiley & Sons, 1996), both incorporated herein by reference).

In one embodiment, compositions of the present invention comprise the indicated agent, while in another embodiment, compositions of the present invention consist essentially of the indicated agent, while in another embodiment, compositions of the present invention consist of the indicated agent. In some embodiments, the term "comprise" refers to the inclusion of the indicated active agent, such as human fibroblast growth factor-9 polypeptide, shh, wnt, etc, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In one embodiment, methods of the present invention treat, inhibit or suppress hair loss. In one embodiment, methods of the present invention generate hair follicles or increase hair follicle size, in one embodiment, in a subject with hair loss. In one embodiment, hair loss is due to androgenetic alopecia (AGA). In another embodiment, hair loss is due to male pattern baldness. In another embodiment, hair loss is due to female pattern baldness. In another embodiment, hair loss is the result of a skin injury.

In another embodiment, the methods of the present invention treat, inhibit, or suppress a disease or disorder in a subject. In one embodiment, the subject has a disease or disorder comprising balding. In another embodiment, the subject does not have a disease or disorder comprising balding. In another embodiment, the disease or disorder is androgenetic alopecia (AGA). In another embodiment, the disease or disorder is male pattern baldness. In another embodiment, the disease or disorder is female pattern baldness. In another embodiment, the disease or disorder is a discoid lupus erythematosis. In another embodiment, the disease or disorder is a congenital hypotrichosis. In another embodiment, the disease or disorder is a lichen planopilaris.

In another embodiment, the disease or disorder is a scarring (or, in another embodiment, cicatricial) alopecia, which in one embodiment, is hair loss due to scarring of the scalp area. In one embodiment, scarring alopecia typically involves the top of the scalp and occurs predominantly in women. The condition frequently occurs in African-American women and is believed to be associated with persistent tight braiding or "corn-rowing" of scalp hair. A form of scarring alopecia also may occur in post-menopausal women, associated with inflammation of hair follicles and subsequent scarring. In another embodiment, the disease or disorder is any other disease or disorder comprising balding known in the art.

In another embodiment, the present invention provides methods for treating Alopecia greata, which in one embodiment, is an autoimmune disorder that causes patchy hair loss that can range from diffuse thinning to extensive areas of baldness with "islands" of retained hair.

In another embodiment, the present invention provides methods for treating Trichotillomania, which in one embodiment, compulsive hair pulling. Hair loss due to trichotillomania is typically patchy, as compulsive hair pullers tend to concentrate the pulling in selected areas.

In another embodiment, the present invention provides methods for treating Triangular alopecia, which in one embodiment, is a loss of hair in the temporal areas that sometimes begins in childhood. Hair loss may be complete, or a few fine, thin-diameter hairs may remain.

In another embodiment, the present invention provides methods for treating Telogen effluvium, which in one embodiment, is a common type of hair loss caused when a large percentage of scalp hairs are shifted into "shedding" phase. The causes of telogen effluvium may be hormonal, nutritional, drug-associated, or stress-associated.

In another embodiment, the present invention provides methods for treating Loose-anagen syndrome, which in one embodiment, is a condition occurring primarily in fair-haired persons in which scalp hair sits loosely in hair follicles and is easily extracted by combing or pulling. In one embodiment, the condition may appear in childhood.

In another embodiment, the present invention provides methods for treating Tinea to Capitis (Scalp Ringworm), which in one embodiment, is caused by a fungal infection, and in one embodiment, is characterized by patches of scaling that can spread and result in broken hair, redness, swelling, and oozing on the scalp.

In another embodiment, the present invention provides methods for treating hair loss associated with particular conditions, which in one embodiment, is cancer, thyroid disease, inadequate protein in diet, low serum iron levels, or associated with particular environmental stimuli, which in one embodiment, is chemotherapy, or, in another embodiment, radiotherapy.

In other embodiments, the present invention provides a method of treating any disease, disorder, or symptom associated with balding. In other embodiments, the present invention provides a method of treating any disease, disorder, or symptom associated with degenerative skin disorder. In other embodiments, the present invention provides a method of treating any disease, disorder, or symptom associated with alopecia. Each disease, disorder, or symptom represents a separate embodiment of the present invention.

In one embodiment, "treating" refers to either therapeutic treatment or prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse, decreasing the number or frequency of relapse episodes, increasing latency between symptomatic episodes, or a combination thereof. In one embodiment, "suppressing" or "inhibiting", refers inter alia to reducing the severity of symptoms, reducing the severity of the current episode, reducing the number of symptoms, reducing the incidence of symptoms, reducing the latency of symptoms, ameliorating symptoms, reducing secondary symptoms, reducing secondary infections, or a combination thereof.

In one embodiment, symptoms are primary, while in another embodiment, symptoms are secondary. In one embodiment, "primary" refers to a symptom that is a direct result of the alopecia, while in one embodiment, "secondary" refers to a symptom that is derived from or consequent to a primary cause. In one embodiment, the compositions and strains for use in the present invention treat primary or secondary symptoms or secondary complications related to alopecia, in one embodiment, seborrheic dermatitis.

In another embodiment, "symptoms" may be any manifestation of alopecia, comprising hair loss, balding, temporary hair loss, patchy hair loss, degenerative skin disorders or a combination thereof.

Methods of determining the presence and severity of alopecia and/or degenerative skin disorders such as those described herein are well known in the art. Each method represents a separate embodiment of the present invention.

In one embodiment, the methods of the present invention are for treating a subject with hair loss. In one embodiment, the hair loss is in the scalp of the subject. In another embodiment, the hair loss is in the eyebrow of the subject. In another embodiment, the hair loss is in scarred skin tissue of the subject, which in one embodiment, may be scalp, eyebrow, arm, or leg of a subject. In another embodiment, any other hair-bearing area or region of the skin is treated by a method of the present invention. Each possibility represents a separate embodiment of the present invention.

In one embodiment, methods of the present invention comprise the step of disrupting the epidermis in the region of said hair loss prior to said administering step. In another embodiment, the epithelium is disrupted.

In another embodiment of methods and compositions of the present invention, the first step (e.g. epidermal disruption) is performed 3-12 days prior to the second step (e.g. addition of an active compound, factor, cell, etc). In another embodiment, the interval is 4-12 days. In another embodiment, the interval is 5-12 days. In another embodiment, the interval is 4-11 days. In another embodiment, the interval is 6-11 days. In another embodiment, the interval is 6-10 days. In another embodiment, the interval is 6-9 days. In another embodiment, the interval is 6-8 days. In another embodiment, the interval is 7-8 days. In another embodiment, the interval is 5-11 days. In another embodiment, the interval is 5-10 days. In another embodiment, the interval is 7-10 days. In another embodiment, the interval is about 1 week. In another embodiment, the compositions for use in the methods of the present invention are applied as the scabbing starts to heal, which in one embodiment is 3-12 days after epidermal disruption. In one embodiment, the compositions for use in the methods of the present invention are applied one day after scab detachment, in another embodiment, two days after scab detachment, in another embodiment, three days after scab detachment, in another embodiment, four days after scab detachment, in another embodiment, five days after scab detachment, in another embodiment, six days after scab detachment, in another embodiment, seven days or more after scab detachment. In another embodiment, the compositions for use in the present invention are administered on days 1-4 after scab detachment. Each possibility represents a separate embodiment of the present invention.

In one embodiment, the step of disrupting is performed by exposing the region of said hair loss to a mechanical, chemical, or optical stimulus. In one embodiment, the optical stimulus is radiation.

The step of disrupting the epidermis in methods of the present invention is performed, in another embodiment, by abrading the skin region of interest. In another embodiment, the term "abrading" refers to an act of creating an abrasion. In another embodiment, "abrading" refers to rubbing. In another embodiment, "abrading" refers to wearing away by friction. In one embodiment, epidermal abrasion causes, under the conditions utilized herein, de novo HF neo-genesis. In another embodiment, the epidermal layer is disrupted.

In one embodiment, "abrasion" refers to a wound consisting of superficial damage to the skin. In another embodiment, "abrasion" refers to an area of the scalp or skin from which the epidermis is removed. In another embodiment, "abrasion" refers to an area of the scalp or skin from which the epidermis and dermis are removed. Each definition of "abrading" and "abrasion" represents a separate embodiment of the present invention.

In one embodiment, epidermal disruption by a method of the present invention converts the skin region of interest back to an embryonic-like state, in which the follicle regenerates. In another embodiment, a subsequent window of opportunity is created, during which the number and size of new HF in the skin region of interest can be manipulated. In another embodiment, the administration of a compound or factor that promotes a differentiation of an uncommitted epidermal cell into a HF cell during this window causes regeneration of larger and more numerous HF. In one embodiment, the morphology of HF in abraded skin is similar to that of embryonic HF, and the markers expressed are similar as well.

In another embodiment, the excisional wounds of methods of the present invention are created using a surgical tool. In one embodiment, the surgical tool is a dermal biopsy punch. In another embodiment, the excisional wounds are induced by freezing or cryoinjury. The use of freezing or cryoinjury is well known in the art, and is used, for example by dermatologists to injure skin. In one embodiment, the freezing or cryoinjury results in a blister. In another embodiment, the blister is used as a "chamber" to introduce drugs and or cells into the reepithelialized area. Each possibility represents a separate embodiment of the present invention.

In another embodiment, the epidermal disruption in methods of the present invention further removes dermal tissue from the skin region of interest. In another embodiment, the epidermal disruption does not remove dermal tissue from the skin region of interest. Each possibility represents a separate embodiment of the present invention.

"Disrupting" an epidermis or epidermal layer refers, in another embodiment, to removing part of the epidermis or epidermal layer. In another embodiment, the term refers to disturbing the intactness of the epidermis or epidermal layer. In another embodiment, the term refers to perforating the epidermis or epidermal layer. In another embodiment, only part of the epidermal layer need be removed. In another embodiment, the entire epidermal layer is removed. In another embodiment, the term refers to abrading the epidermis or epidermal layer. In another embodiment, the term refers to wounding the epidermis or epidermal layer. Each possibility represents a separate embodiment of the present invention.

In another embodiment, the epidermal disruption is performed with a tool that comprises sandpaper. In another embodiment, the epidermal disruption is performed with a laser. In another embodiment, the laser is a Fraxel laser. In another embodiment, the laser is a $CO_2$ laser. In another embodiment, the laser is an excimer laser. In another embodiment, the laser is any other type of laser capable of inducing trans-epithelial injury. In another embodiment, the epidermal disruption is performed with a felt wheel. In another embodiment, the epidermal disruption is performed with a surgical tool. In another embodiment, the epidermal disruption is performed with any other tool known in the art that is capable of epidermal disruption. In another embodiment, the epidermal disruption comprises use of a micro-dermabrasion device. In another embodiment, the epidermal disruption comprises a burn treatment.

In another embodiment, the epidermal disruption comprises a disruption of a follicle of said epidermis and a disruption of an interfollicular region of said epidermis. In another embodiment, the epidermal disruption comprises a disruption of a follicle of said epidermis and does not comprise a disruption of an interfollicular region of said epidermis. Each possibility represents a separate embodiment of the present invention.

In another embodiment, the epidermal disruption comprises a light-based method. In another embodiment, the epidermal disruption comprises irradiation with visible light. In another embodiment, the epidermal disruption comprises irradiation with infrared light. In another embodiment, the epidermal disruption comprises irradiation with ultraviolet radiation. In another embodiment, the epidermal disruption comprises orthovoltage irradiation. In another embodiment, the epidermal disruption comprises X-ray irradiation. In another embodiment, the epidermal disruption comprises any other type of irradiation known in the art.

In another embodiment, the epidermal disruption is performed by mechanical means. In another embodiment, "mechanical means" refers to abrading. In another embodiment, the term refers to wounding. In another embodiment, the term refers to ultrasound. In another embodiment, the term refers to radio-frequency. In another embodiment, the term refers to an electrical process or the use of an electrical current. In another embodiment, the term refers to electoporation. In another embodiment, the term refers to excision. In another embodiment, the term refers to tape-stripping. In another embodiment, the term refers to microdermabrasion. In another embodiment, the term refers to the use of peels. In another embodiment, the term refers to any other type of mechanical means known in the art. Each possibility represents a separate embodiment of the present invention.

In another embodiment, the epidermal disruption comprises chemical treatment. In another embodiment, the chemical is phenol. In another embodiment, the chemical is trichloracetic acid. In another embodiment, the chemical is ascorbic acid. In another embodiment, the chemical is any other chemical capable of epidermal disruption that is known in the art.

In another embodiment, epidermal trauma is utilized in a method of the present invention.

Each method or type of epidermal disruption, abrasion, and trauma represents a separate embodiment of the present invention.

In one embodiment, "WIHN" refers to HF neogenesis induced by disruption of the epithelial layer. In another embodiment, the term refers to HF neogenesis induced by abrasion. In another embodiment, the term refers to HF neogenesis induced by wounding. In another embodiment, the term refers to HF neogenesis induced by disruption of the epithelial layer, followed by administration of a compound or factor that promotes a differentiation of an uncommitted epidermal cell into a HF cell. Each possibility represents a separate embodiment of the present invention.

In another embodiment, the epidermal disruption of methods of the present invention creates an abrasion at least about 1-1.5 centimeters (cm) in width. In another embodiment, the abrasion is at least about 1 cm in width. In another embodiment, the abrasion is at least about 1.5 cm in width. In another embodiment, the abrasion is at least about 2 cm in width. Each type of abrasion represents a separate embodiment of the present invention.

In another embodiment, the excisional wounds of methods of the present invention are not surgically closed. In another embodiment, the excisional wounds are allowed to heal by secondary intention. In another embodiment, the skin region of interest is not contacted with a bandage or dressing following the epidermal disruption. In another embodiment, the skin region of interest is not contacted with an ointment following the epidermal disruption. In another embodiment, the skin region of interest is allowed to heal for a period of time without being contacted by any substance, device, ointment, etc., that is ordinarily administered to an abrasion or wound to facilitate healing. In another embodiment, the skin region of interest is allowed to heal for a period of time without being contacted by any substance, device, ointment, etc., that is ordinarily administered to an abrasion or wound to prevent infection. In another embodiment, the "period of time" is the time it takes the epidermal disruption to heal. In another embodiment, the period of time is any time or range of times between 2 days and 3 weeks. Each possibility represents a separate embodiment of the present invention.

In one embodiment, "following" refers to a period of time of about 2 days. In another embodiment, "following" refers to a period of time of about 3 days. In another embodiment, "following" refers to a period of time of about 4 days. In another embodiment, "following" refers to a period of time of about 5 days. In another embodiment, "following" refers to a period of time of about 7 days. In another embodiment, "following" refers to a period of time of about 10 days. In another embodiment, "following" refers to a period of time of about 2 weeks. In another embodiment, "following" refers to a period of time of about 3 weeks. Each possibility represents a separate embodiment of the present invention.

In another embodiment, a method of the present invention further comprises the step of depilating the skin in the region in which hair growth or follicle formation is desired. In one embodiment, said step of depilating is performed prior to said step of epidermal disruption.

In another embodiment, the depilation is epilation. In another embodiment, the depilation comprises the step of waxing. In another embodiment, the depilation comprises the step of plucking. In another embodiment, the depilation comprises the use of an abrasive material. In another embodiment, the depilation comprises the use of a laser. In another embodiment, the depilation comprises the use of electrolysis. In another embodiment, the depilation comprises the use of a mechanical device. In another embodiment, the depilation comprises the use of thioglycolic acid. In another embodiment, the depilation comprises the use of any other method of depilation or epilation known in the art. Each possibility represents a separate embodiment of the present invention.

In another embodiment, the additional step (depilation or administration of a retinoid) is performed prior to the step of disrupting the epidermis. In another embodiment, the additional step is performed following the step of disrupting the epidermis, but prior to the addition of the compound or factor that of the present invention. In another embodiment, the additional step is performed concurrently with the addition of the differentiation-promoting compound or factor. In another embodiment, the additional step is performed following the addition of the differentiation-promoting compound or factor. Each possibility represents a separate embodiment of the present invention.

In another embodiment, a method of the present invention further comprises the step of administering a topical retinoid to the skin region of interest. In one embodiment, the topical retinoid induces resting (telogen) HF in the skin region of interest to enter anagen. Each possibility represents a separate embodiment of the present invention.

In another embodiment, the additional step is performed between about two days and about three weeks before the step of abrading. In another embodiment, the additional step is performed about two days before the step of abrading. In another embodiment, the additional step is performed about three days before the step of abrading. In another embodiment, the additional step is performed about four days before the step of abrading. In another embodiment, the additional step is performed about one week before the step of abrading. In another embodiment, the additional step is performed about ten days before the step of abrading. In another embodiment, the additional step is performed about two weeks before the step of abrading. In another embodiment, the additional step is performed about three weeks before the step of abrading. Each possibility represents a separate embodiment of the present invention.

In one embodiment, the methods of the present invention further comprise the step of administering an antagonist of an androgen or an antagonist of an androgen receptor. In another embodiment, the methods of the present invention further comprise the step of administering a 5 alpha-reductase type 2 inhibitor.

In another embodiment, a method of the present invention further comprises the step of contacting the skin region of interest with an anti-androgen compound. In one embodiment, the anti-androgen compound is finasteride. In another embodiment, the anti-androgen compound is Fluridil®. In another embodiment, the anti-androgen compound is dutasteride. In another embodiment, the anti-androgen compound is spironolactone. In another embodiment, the anti-androgen compound is cyproterone acetate. In another embodiment, the anti-androgen compound is bicalutamide. In another embodiment, the anti-androgen compound is flutamide. In another embodiment, the anti-androgen compound is nilutamide. In another embodiment, the anti-androgen compound is an inhibitor of an androgen receptor. In another embodiment, the anti-androgen compound is any other anti-androgen compound known in the art. Each possibility represents a separate embodiment of the present invention.

In another embodiment, a method of the present invention further comprises the step of contacting the skin region of interest with an estrogen compound. In another embodiment, a method of the present invention further comprises the step of contacting the skin region of interest with an estrogen receptor agonist. In another embodiment, a method of the present invention further comprises the step of contacting the skin region of interest with an estrogen analogue. In one embodiment, the estrogen analogue is estradiol. In another embodiment, the estrogen analogue is 17 beta-estradiol. In another embodiment, the estrogen analogue is 17 alpha-estradiol. In another embodiment, the estrogen analogue is ZYC3. In another embodiment, the estrogen compound, estrogen receptor agonist, or estrogen analogue is any other estrogen compound, estrogen receptor agonist, or estrogen analogue known in the art. Each possibility represents a separate embodiment of the present invention.

In another embodiment, a method of the present invention further comprises the step of contacting the skin region of interest with an inhibitor of an EGF protein. In another embodiment, a method of the present invention further comprises the step of contacting the skin region of interest with an inhibitor of an EGFR. In another embodiment, a method of the present invention further comprises the step of contacting the skin region of interest with a compound that reduces an expression of an EGF protein or an EGFR. Each possibility represents a separate embodiment of the present invention.

In another embodiment, the inhibitor of an EGF or an EGF receptor is panitumumab. In another embodiment, the inhibitor is AG1478. In another embodiment, the inhibitor is nimotuzumab. In another embodiment, the inhibitor is an antibody that binds EGF or EGFR. In another embodiment, the inhibitor is HuMax-EGFR® (Genmab, Copenhagen, Denmark). In another embodiment, the inhibitor is cetuximab. In another embodiment, the inhibitor is IMC 11F8. In another embodiment, the inhibitor is matuzumab. In another embodiment, the inhibitor is SC 100. In another embodiment, the inhibitor is ALT 110. In another embodiment, the inhibitor is PX 1032. In another embodiment, the inhibitor is BMS 599626. In another embodiment, the inhibitor is MDX 214. In another embodiment, the inhibitor is PX 1041. In another embodiment, the inhibitor is any other inhibitor of an EGF or an EGF receptor known in the art. Each possibility represents a separate embodiment of the present invention.

In another embodiment, a method of the present invention further comprises the step of contacting the skin region of interest with an inhibitor of a tyrosine kinase activity of an EGF receptor. In another embodiment, the inhibitor is gefitinib. In another embodiment, the inhibitor is erlotinib. In another embodiment, the inhibitor is canertinib. In another embodiment, the inhibitor is leflunomide. In another embodiment, the inhibitor is A77 1726. In another embodiment, the inhibitor is pelitinib. In another embodiment, the inhibitor is ZD 1839. In another embodiment, the inhibitor is CL 387785. In another embodiment, the inhibitor is EM 785. In another embodiment, the inhibitor is vandetanib. In another embodiment, the inhibitor is any other inhibitor of a tyrosine kinase activity of an EGF receptor known in the art. Each possibility represents a separate embodiment of the present invention.

In another embodiment, a method of the present invention further comprises the step of contacting the skin region of interest with an EGF or EGFR antagonist. In another embodiment, the EGF or EGFR antagonist is a carboxypeptidase inhibitor from potato (PCI) protein or a homologue, fragment or mimetic thereof. In another embodiment, the EGF or EGFR antagonist is a sprouty protein or a homologue, fragment or mimetic thereof. In another embodiment, the EGF or EGFR antagonist is an Argos protein or a homologue, fragment or mimetic thereof. In another embodiment, the EGF or EGFR antagonist is a lefty protein or a homologue, fragment or mimetic thereof. In another embodiment, the EGF or EGFR antagonist is an antibody that recognizes EGF or EGFR, or a fragment or mimetic thereof. In another embodiment, the EGF or EGFR antagonist is small molecule inhibitor that binds and reduces the activity of EGF or EGFR. In another embodiment, the EGF or EGFR antagonist is CRM197. In another embodiment, the EGF or EGFR antagonist is IMC-C225 (ImClone Systems, New York, N.Y.). In another embodiment, the EGF or EGFR antagonist is any other antagonist of EGF or EGFR known in the art. Each possibility represents a separate embodiment of the present invention.

In another embodiment, the EGF or EGFR antagonist is a carboxypeptidase inhibitor from potato (PCI) protein or a homologue, fragment or mimetic thereof. In another embodiment, the EGF or EGFR antagonist is a sprouty protein or a homologue, fragment or mimetic thereof. In another embodiment, the EGF or EGFR antagonist is an Argos protein or a homologue, fragment or mimetic thereof. In another embodiment, the EGF or EGFR antagonist is a lefty protein or a homologue, fragment or mimetic thereof. In another embodiment, the EGF or EGFR antagonist is an antibody that recognizes EGF or EGFR, or a fragment or mimetic thereof. In another embodiment, the EGF or EGFR antagonist is small molecule inhibitor that binds and reduces the activity of EGF or EGFR. In another embodiment, the EGF or EGFR antagonist is CRM197. In another embodiment, the EGF or EGFR antagonist is IMC-C225 (ImClone Systems, New York, N.Y.). In another embodiment, the EGF or EGFR antagonist is any other antagonist of EGF or EGFR known in the art. Each possibility represents a separate embodiment of the present invention.

The EGFR of methods and compositions of the present invention has, in another embodiment, the sequence: MRPSGTAGAALLALLAALCPASRALEEKKVCQGTSNKLTQLGTFEDHFLSLQRMFNN CEVVLGNLEITYVQRNYDLSFLKTIQEVAGYVLIALNTVERIPLENL QIIRGNMYYENS YALAVLSNYDANKTGLKELPMRNLQEILHGAVRFSNNPALCNVESIQWRDIVSSDFLS NMSMDFQNHLGSCQKCDPSCPNGSCWGAGEENCQKLTKIICAQQCSGRCRGKSPSD CCHNQCAAGCTGPRESDCLVCRKFRDEATCKDTCPPLMLYNPTTYQMDVNPEGKYS FGATCVKKCPRNYVVTDHGSCVRACGADSYEMEEDGVRKCKKCEGPCRKVCNGIGI GEFKDSLSINATNIKHFKNCTSISGDLHILPVAFRGDSFTHTPPLDPQELDILKTVKEITG FLLIQAWPENRTDLHAFENLEIIRGRTKQHGQFSLAVVSLNITSLGLRSLKEISDGDVIIS GNKNLCYANTINWKKLFGTSGQKTKIISNRGENSCKATGQVCHALCSPEGCWGPEPR DCVSCRNVSRGRECVDKCNLLEGEPREFVENSECIQCHPECLPQAMNITCTGRGPDN CIQCAHYIDGPHCVKTCPAGVMGENNTLVWKYADAGHVCHLCHPNCTYGCTGPGL EGCPTNGPKIPSIATGMVGALLLLLVVALGIGLFMRRRHIVRKRTLRRLLQERELVEPL TPSGEAPNQALLRILKETEFKKIKVLGSGAFGTVYKGLWIPEGEKVKIPVAIKELREAT SPKANKEILDEAYVMASVDNPHVCRLLGICLTSTVQLITQLMPFGCLLDYVREHKDNI GSQYLLNWCVQIAKGMNYLEDRRLVHRDLAARNVLVKTPQHVKITDFGLAKLLGAE EKEYHAEGGKVPIKWMALESILHRIYTHQSDVWSYGVTVWELMTFGSKPYDGIPASE ISSILEKGERLPQPPICTIDVYMIMVKCWMIDADSRPKFRELIIEFSKMARDPQRYLVIQ GDERMHLPSPTDSNFYRALMDEEDMDDVVDADEYLIPQQGFFSSPSTSRTPLLSSLSA TSNNSTVACIDRNGLQSCPIKEDSFLQRYSSDPTGALTEDSIDDTFLPVPEYINQSVPKR PAGSVQNPVYHNQPLNPAPSRDPHYQDPHSTAVGNPEYLNTVQPTCVNSTFDSPAH WAQKGSHQISLDNPDYQQDFFPKEAKPNGIFKGSTAENAEYLRVAPQSSEFIGA (GenBank Accession No: NM_005228; SEQ ID No: 8). In another embodiment, the EGFR has a sequence selected from the sequences set forth in GenBank entries NM_201282, NM_201283, NM_201284, BC094761, AF288738, AY588246, AY573061, X17054, AF125253, U48722, K03193, and AY698024. In another embodiment, the EGFR is encoded by a nucleic acid molecule having a sequence set forth in the one of the above GenBank entries. In another embodiment, a biologically active fragment of an EGFR is utilized in a method of the present invention. Each possibility represents a separate embodiment of the present invention.

The EGF of methods and compositions of the present invention has, in another embodiment, the sequence: MLLTLIILLPVVSKFSFVSLSAPQHWSCPEGTLAGNGNSTCVGPAPFLIFSHGNSIFRIDT EGTNYEQLVVDAGVSVIMDFHYNEKRIYWVDLERQLLQRVFLNGSRQERVCNIEKNV SGMAINWINEEVIWSNQQEGIITVTDMKGNNSILLSALKYPANVAVDPVERFIFWSSE VAGSLYRADLDGVGVKALLETSEKITAVSLDVLDKRLFWIQYNREGSNSLICSCDYDG GSVHISKHPTQHNLFAMSLFGDRIFYSTWKMKTIWIANKHTGKDMVRINLHSSFVPLG ELKVVHPLAQPKAEDDTWEPEQKLCKLRKGNCSSTVCGQDLQSHLCMCAEGYALSR DRKYCEDVNECAFWNHGCTLGCKNTPGSYYCTCPVGFVLLPDGKRCHQLVSCPRNV SECSHDCVLTSEGPLCFCPEGSVLERDGKTCSGCSSPDNGGCSQLCVPLSPVSWECDCF PGYDLQLDEKSCAASGPQPFLLFANSQDIRHMHFDGTDYGTLLSQQMGMVYALDHDP VENKIYFAHTALKWIERANMDGSQRERLIEEGVDVPEGLAVDWIGRRFYWTDRGKSLI GRSDLNGKRSKIITKENISQPRGIAVHPMAKRLFWTDTGINPRIESSSLQGLGRLVIASSD LIWPSGITIDFLTDKLYWCDAKQSVI- EMANLDGSKRRRLTQNDVGHPFAVAVFEDYV WFSD-WAMPSVIRVNKRTGKDRVRLQGSM-LKPSSLVVVHPLAKPGADPCLYQNGGCE HICKKRLGTAWCSCREGFMKASDGKT-CLALDGHQLLAGGEVDLKNQVTPLDILSKTR VSED-NITESQHMLVAEIMVSDQDDCAPVGCSM-YARCISEGEDATCQCLKGFAGDGKL CSDIDECEMGYPVCPPASSKCINTEG-GYVCRCSEGYQGDGIHCLDIDECQLGVHSCGE NASCTNTEGGYTCMCAGRLSEPGLICPD-STPPPHLREDDHHYSVRNSDSECPLSHDGY CLHDGY-CMYIEALDKYACNCVVGYIGERC-QYRDLKWWELRHAGHGQQQKVIVVAV CVVVLVMLLLLSLWGAHYYRTQKLLSKN-PKNPYEESSRDVRSRRPADTEDGMSSCPQ PWFV-VIKEHQDLKNGGQPVAGEDGQAADGSM-QPTSWRQEPQLCGMGTEQGCWIPVS SDKGSCPQVMERSFHMPSYGTQTLEG-GVEKPHSLLSANPLWQQRALDPPHQMELTQ (Gen-Bank Accession No: NM_001963; SEQ ID No: 9). In another embodiment, the EGF has a sequence selected from the sequences set forth in GenBank entries BC093731, AY548762, and X04571. In another embodiment, the EGF is encoded by a nucleic acid molecule having a sequence set forth in the one of the above GenBank entries. In another embodiment, a biologically active fragment of an EGF is utilized in a method of the present invention. Each possibility represents a separate embodiment of the present invention.

In another embodiment, a method of the present invention further comprises the step of contacting the skin region of interest with a Hedgehog protein. In another embodiment, a method of the present invention further comprises the step of contacting the skin region of interest with a nucleotide encoding a Hedgehog protein. In another embodiment, a method of the present invention further comprises the step of contacting the skin region of interest with an activator of a Hedgehog protein. Each possibility represents a separate embodiment of the present invention.

In one embodiment, the methods of the present invention further comprise the step of administering a 5 alpha-reductase type 2 inhibitor, which in one embodiment, is Finasteride or, in another embodiment, turosteride.

In another embodiment, the methods of the present invention further comprise the step of administering a reductase inhibitor, which in one embodiment is an FCE—dual inhibitor, which in one embodiment is FCE 28260; FCE 28175, or FCE 27837; in another embodiment is an MK inhibitor, which in one embodiment, is MK 0434, MK 0963, or MK 386; in another embodiment, is an FK Nonsteroidal Inhibitor, which in one embodiment is FK 143; and in another embodiment is a LY Nonsteroidal Inhibitor, which in one embodiment, is LY 191704; and in another embodiment, is a SK&F Inhibitor, which in one embodiment, is SK&F 105657.

In another embodiment, the methods of the present invention further comprise the step of administering an additional composition. In one embodiment, the composition is Dutasteride (Avodart®, GI198745), Finasteride (Propecia®, Proscar®), Turosteride, Azelaic acid, Zinc sulphate, CS 891, or a combination thereof.

In another embodiment, the methods of the present invention further comprise the step of administering an antiandrogen, which in one embodiment is Spironolactone (Aldactone®), Flutamide (Euflex®, Eulexin®), Casodex, Inocoterone, an RU Antiandrogen, TZP-4238, Win 49596, Fluridil (Eucapil®), or a combination thereof.

In another embodiment, the methods of the present invention further comprise the step of administering a K+ Channel Opener, which in one embodiment, is minoxidil (Rogaine®), Diazoxide, Cromakalim, Pinacidil, or a combination thereof.

In another embodiment, the methods of the present invention further comprise the step of administering a vasodilator, which in one embodiment, is minoxidil (Rogaine®).

In another embodiment, the methods of the present invention further comprise the step of administering an estrogen blocker, which in one embodiment, is an ICI Estrogen Blocker.

The subject of methods of the present invention, is, in another embodiment, a human. In another embodiment, the subject is a rodent, in one embodiment, a mouse, in another embodiment, a rat. In another embodiment, the subject is a mammal. In another embodiment, the subject is a vertebrate. In another embodiment, the subject is feline, canine, ovine, or bovine. In another embodiment, the subject is a male. In another embodiment, the subject is a female. In another embodiment, the subject is any other subject known in the art. Each possibility represents a separate embodiment of the present invention.

In another embodiment, the subject is an adult. In one embodiment, "adult" refers to an age greater than about 18 years. In another embodiment, "adult" refers to an age greater than about 20 years. In another embodiment, "adult" refers to an age greater than about 25 years. In another embodiment, "adult" refers to an age greater than about 30 years. In another embodiment, "adult" refers to an age greater than about 35 years. In another embodiment, "adult" refers to an age greater than about 40 years. In another embodiment, "adult" refers to an age greater than about 45 years.

In another embodiment, the subject is elderly. In one embodiment, "elderly" refers to an age greater than about 45 years. In another embodiment, "elderly" refers to an age greater than about 50 years. In another embodiment, "elderly" refers to an age greater than about 55 years. In another embodiment, "elderly" refers to an age greater than about 60 years. In another embodiment, "elderly" refers to an age greater than about 65 years. In another embodiment, "elderly" refers to an age greater than about 70 years.

In another embodiment, the first subject, or, where applicable, both the first subject and the second subject, is a laboratory animal. In another embodiment, the subject(s) is/are mice. In another embodiment, the subject(s) is/are rats. In another embodiment, the subject(s) is/are gerbils. In another embodiment, the subject(s) is/are hamsters. In another embodiment, the subject(s) is/are guinea pigs. In another embodiment, the subject(s) is/are rabbits. In another embodiment, the subject(s) is/are pigs. In another embodiment, the subject(s) is/are dogs. In another embodiment, the subject(s) is/are cats. In another embodiment, the subject(s) is/are primates. In another embodiment, the subject(s) is/are any other laboratory animal known in the art. Each possibility represents a separate embodiment of the present invention.

In one embodiment, the subject is contacted with FGF9, or in another embodiment, with a composition comprising FGF9. In another embodiment, FGF9 or a composition comprising FGF9 is administered to a subject.

"Contacting" as used herein refers, in another embodiment, to bringing skin, in one embodiment, scalp, eyebrow, etc, into to contact with a compound, factor, cell, etc. In another embodiment, the term refers to embedding the compound, factor, cell, etc into the skin region of interest. In another embodiment, the term refers to injecting the compound, factor, cell, etc into the skin region of interest. In another embodiment, term refers to any other type of contacting known in the art. Each possibility represents a separate embodiment of the present invention.

In another embodiment, the step of contacting in methods of the present invention comprises directly contacting the skin region of interest with the compound, RNA, protein, etc. In another embodiment, the step of contacting comprises indirectly contacting the skin region of interest via contacting another site or tissue of the subject, after which the compound, RNA, or protein is transported to the skin region of interest by a biological process; e.g, diffusion, active transport, or circulation in a fluid such as the blood, lymph, interstitial fluid, etc. Each possibility represents a separate embodiment of the present invention.

In one embodiment, other fibroblast growth factors may be used in the methods of the present invention. In one embodiment, FGF1, FGF2, FGF3, FGF4, FGF5, FGF6, FGF7, FGF8, FGF9, FGF10, or a combination thereof may be used in the methods of the present invention. In one embodiment, FGF1 through FGF10 all bind fibroblast growth factor receptors (FGFRs). In one embodiment, FGF1 is known as acidic fibroblast growth factor, and FGF2 is also known as basic fibroblast growth factor.

In another embodiment, FGF11, FGF12, FGF13, or FGF14, may be used in the methods of the present invention. In one embodiment, FGF11, FGF12, FGF13, and FGF14 are known as FGF homologous factors 1-4 (FHF1-FHF4), and in another embodiment, have distinct functional differences compared to the FGFs. In one embodiment, these factors possess remarkably similar sequence homology, they do not in one embodiment, bind FGFRs and are involved in intracellular processes unrelated to the FGFs. In one embodiment, this group is also known as "iFGF".

In another embodiment, FGF16, FGF17, FGF18, FGF19, FGF20, FGF21, FGF22, or FGF23 may be used in the methods of the present invention. In one embodiment, FGF15/FGF19, FGF21 and FGF23 have systemic rather than local effects.

Pharmaceutical Compositions

In another embodiment, methods of the present invention comprise administering a pharmaceutical composition comprising FGF9 or an up-regulator of SHH and/or its analog, derivative, isomer, metabolite, pharmaceutically acceptable salt, pharmaceutical product, hydrate, N-oxide, or any combination thereof; and a pharmaceutically acceptable carrier. Each possibility represents a separate embodiment of the present invention.

The pharmaceutical compositions containing FGF9 or an up-regulator of SHH can, in another embodiment, be administered to a subject by any method known to a person skilled in the art, such as topically, parenterally, paracancerally, transmucosally, transdermally, intramuscularly, intravenously, intradermally, subcutaneously, subepidermally, intraperitonealy, intraventricularly, intra-arteriolly, intravascularly, intracranially, intravaginally, intrarectally, or intratumorally. Each possibility represents a separate embodiment of the present invention. In one embodiment, the dosage regimen will be determined by skilled clinicians, based on factors such as exact nature of the condition being treated, the severity of the condition, the age and general physical condition of the patient, body weight, and response of the individual patient, etc.

In another embodiment, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the FGF9 or other polypeptide as provided herein composition is formulated in a capsule. In another embodiment, the compositions of the present invention comprise, in addition to FGF9 or other polypeptide as provided herein an inert carrier or diluent, or a hard gelating capsule.

In another embodiment, the pharmaceutical compositions are administered topically to body surfaces and are thus formulated in a form suitable for topical administration. Suitable topical formulations include gels, ointments, creams, lotions, drops, gels; pastes; powders; aerosol sprays; syrups or ointments on sponges or cotton applicators; and solutions or suspensions in an aqueous liquid, non-aqueous liquid, oil-in-water emulsion, or water-in-oil liquid emulsion, and the like. Because of its ease of administration, a cream, lotion, or ointment represents the most advantageous topical dosage unit form, in which case liquid pharmaceutical carriers may be employed in the composition. These creams, lotions, or ointments, may be prepared as rinse-off or leave-on products, as well as two stage treatment products for use with other skin cleansing or managing compositions. In a preferred embodiment, the compositions are administered as a rinse-off product in a higher concentration form, such as a gel, and then a leave-on product in a lower concentration to avoid irritation of the skin. Each of these forms is well understood by those of ordinary skill in the art, such that dosages may be easily prepared to incorporate the pharmaceutical composition of the invention. In one embodiment, a delayed release patch may be used for administration of FGF9. For topical administration, the FGF9 composition or its physiologically tolerated derivatives such as salts, esters, N-oxides, and the like are prepared and applied as solutions, suspensions, or emulsions in a physiologically acceptable diluent with or without a pharmaceutical carrier.

Ointment preparations may be roughly classified into fat/oil type ointments, emulsified ointments, water-soluble ointments and suspended ointments according to the type of the base (vehicle) used therefor. An ointment may comprise, for example, fats, fatty oils, lanolin, vaseline, paraffins, waxes, resins, plastics, glycols, higher alcohols, glycerol, water, emulsifiers, suspending agents or other appropriate additives as a diluent, carrier or as a vehicle. Manufacture of an ointment comprises, for example, adding the compound of the present invention to the appropriate additives, diluents, carriers or vehicles followed by mixing to make the mixture homogeneous.

For parenteral application, particularly suitable are injectable, sterile solutions, preferably oily or aqueous solutions, as well as suspensions, emulsions, or implants, including suppositories and enemas. Ampoules are convenient unit dosages. Such a suppository may comprise any agent described herein.

For application by inhalation, solutions or suspensions of the compounds mixed and aerosolized or nebulized in the presence of the appropriate carrier suitable. Such an aerosol may comprise any agent described herein.

For enteral application, particularly suitable are tablets, dragees, liquids, drops, or capsules. In one embodiment, a sweetened vehicle is employed when a syrup, elixir, or the like is used for enteral application.

For liquid formulations, pharmaceutically acceptable carriers are, in another embodiment, aqueous or non-aqueous solutions, suspensions, emulsions or oils. Examples of non-aqueous solvents are propylene glycol, polyethylene glycol, and injectable organic esters such as ethyl oleate. Aqueous carriers include, in another embodiment, water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

In another embodiment, the pharmaceutical compositions are administered by subcutaneous implantation of a pellet. In another embodiment, the pellet provides for controlled release of the FGF9 over a period of time.

In one embodiment, the pharmaceutical compositions are controlled-release compositions, i.e. compositions in which the FGF9 composition is released over a period of time after administration. Controlled- or sustained-release compositions include, in another embodiment, formulation in lipophilic depots (e.g. fatty acids, waxes, oils). In another embodiment, the composition is an immediate-release composition, i.e. a composition in which all the FGF9 composition is released immediately after administration. Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilisates obtained, for example, for the preparation of products for injection.

In one embodiment, compositions of this invention are pharmaceutically acceptable. In one embodiment, the term "pharmaceutically acceptable" refers to any formulation which is safe, and provides the appropriate delivery for the desired route of administration of an effective amount of at least one compound for use in the present invention. This term refers to the use of buffered formulations as well, wherein the pH is maintained at a particular desired value, ranging from pH 4.0 to pH 9.0, in accordance with the stability of the compounds and route of administration.

In one embodiment, FGF9 or upregulators of SHH used in the methods of this invention may be administered alone or within a composition. In another embodiment, compositions comprising FGF9 or upregulators of SHH in admixture with conventional excipients, i.e. pharmaceutically acceptable organic or inorganic carrier substances suitable for parenteral, enteral (e.g., oral) or topical application which do not deleteriously react with the active compounds may be used. In one embodiment, suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. In another embodiment, the pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In another embodiment, they can also be combined where desired with other active agents, e.g., vitamins.

In one embodiment, the therapeutic compositions of the present invention comprise an FGF9 composition and one or more additional compounds effective in preventing or treating dermatologic conditions such as alopecia. In one embodiment, the additional compound is a moisturizer or an emollient, which in one embodiment is petrolatum, white petrolatum, hydrogenated vegetable oil, hydrophilic petrolatum, panthenol, primrose oil, omega-3 fish oils, omega-6 fish oils, linoleic acid, flax seed oil, ceramide, borage oil (linoleic acid), tocopherol (Vitamin E), tocopherol linoleate, dimethicone, glycerine or a combination thereof. In one embodiment, moisturizers improve the ability of the skin to absorb other administered compounds, including inter alia, the compounds for use in the present invention. In another embodiment, moisturizing agents minimize or prevent the skin from drying and cracking, thereby decreasing susceptibility of skin to environmental factors that generate free radicals, thereby preventing additional damage to the skin.

In another embodiment, the additional compound is a topical steroid, which in one embodiment is hydrocortisone, in one embodiment 1% hydrocortisone, triamcinolone, fluocinolone acetonide, halcinonide, halobetasol propionate, clobetasol propionate, betamethasone dipropionate, betamethasone valerate, and triamcinolone acetonide or a combination thereof; oral steroids; topical immunomodulators including, inter alia, tacrolimus, pimecrolimus, Ascomycin, cyclosporine, or a combination thereof; antihistamines, which in one embodiment is hydroxyzine or diphenhydramine hydrochloride, Ketotifen, Doxepin; biologics, which in one embodiment comprises Amevive (alefacept), Enbrel, Humira, Raptiva, Remicade, or a combination thereof; or a combination thereof. In another embodiment, the additional compound is an antibiotic, which in one embodiment comprise tetracycline, doxycline, minocycline, cloxacillin, cephalexin, penicillin, clindamycin or a combination thereof. In another embodiment, the additional compound is methotrexate, tar, coal tar, anthralin, dovonex, salicyclic acid, tazorac, moisturizers, aloe vera, soriatane, accutane, hydrea, mycophenolate mofetil, sulfasalazine, 6-thioguanine, or a combination thereof. In another embodiment, additional compounds comprise acyclovir, which in one embodiment is particularly effective in patients with eczema herpeticum. In one embodiment, additional compounds to treat seborrheic dermatitis comprise zinc pyrithione, selenium sulfide, sulfur, tar shampoo, flucinolone acetonide solution, triamcinolone acetonide lotion, ketoconazole cream, other imidazoles, or a combination thereof.

In another embodiment, the additional compound is an anti-inflammatory agent, which in one embodiment comprises aspirin, ibuprofen, ketoprofen, naproxen, or a combination thereof. In another embodiment, the additional compound is a prostaglandin or prostaglandin inhibitor, which in one embodiment is an inhibitor of PGD2.

In another embodiment, the additional compound is an exfoliant, which in one embodiment comprises an enzymatic exfoliant or a mono- or -poly-hydroxy acid. In one embodiment, the exfoliant is an alpha-hydroxy acid, beta-hydroxy acid, tannic acid, glycolic acid, lactic acid, citric acid, salicylic acid, or a combination thereof. In another embodiment, the additional compound is an analgesic, or anesthetic, while in another embodiment it is aloe vera gel, aloe vera, licorice extract, pilewort, Canadian willow root, zinc, allantoin, or a combination thereof. In another embodiment, the additional compound is an anti-oxidant.

In one embodiment, fibroblast growth factor-9 protein is administered at a concentration of 10 ng/mL. In another embodiment, fibroblast growth factor-9 protein is administered at a concentration of 20 ng/mL. In another embodiment, fibroblast growth factor-9 protein is administered at a concentration of 40 ng/mL. In another embodiment, fibroblast growth factor-9 protein is administered at a concentration of 80 ng/mL. In another embodiment, fibroblast growth factor-9 protein is administered at a concentration of 5 ng/mL. In another embodiment, fibroblast growth factor-9 protein is administered at a concentration of 3 ng/mL. In another embodiment, fibroblast growth factor-9 protein is administered at a concentration of 1 ng/mL. In another embodiment, fibroblast growth factor-9 protein is administered at a concentration of between 1 and 50 ng/mL. In another embodiment, fibroblast growth factor-9 protein is administered at a concentration of between 1 and 15 ng/mL. Each dose represents a separate embodiment.

In general, the doses utilized for the above described purposes will vary, but will be in an effective amount to exert the desired effect. As used herein, the term "pharmaceutically effective amount" refers to an amount of a FGF9 or other composition for use in the present invention, which will produce the desired alleviation in symptoms or other desired phenotype in a patient. The doses utilized for any of the above-described purposes will generally be from 1 to about 1000 milligrams per kilogram of body weight (mg/kg), administered one to four times per day, or by continuous IV infusion. In one embodiment, a topical daily dose range, in single or divided doses, for the conditions described herein is from about 1 mg to 20,000 mg, more preferably about 2,000 mg to 16,000 mg, and most preferably about 6,000 mg to 10,000 mg of the active components (i.e., excluding excipients and carriers). When the compositions are dosed topically or intraocularly, they will generally be in a concentration range of from 0.1 to about 10% w/v, administered 1-4 times per day. In one embodiment, the compositions for use in the methods of the present invention are administered topically two times a day.

In one embodiment of the invention, the concentrations of the compounds will depend on various factors, including the nature of the condition to be treated, the condition of the patient, the route of administration and the individual tolerability of the compositions.

In one embodiment, the administering step is via topical administration. In another embodiment, the administering step is via subcutaneous administration.

In one embodiment, the compound administered as part of methods of the present invention is administered systemically. In another embodiment, the compound is administered topically. In another embodiment, the compound is administered subepidermally. In another embodiment, the compound is administered subcutaneously. In another embodiment, the compound is administered transdermally. In another embodiment, the compound is administered to the site of the abrasion. In another embodiment, the compound is administered to the site of the wound induction. In another embodiment, the compound is administered to the site of the depilation. In another embodiment, the compound is administered during wound healing. In another embodiment, the compound is administered prior to HF neo-genesis. In another embodiment, the compound is administered during HF neo-genesis. Each possibility represents a separate embodiment of the present invention.

In one embodiment, the route of administration may be directed to an organ or system that is affected by alopecia. For example, compounds may be administered topically to treat dermatologic conditions such as alopecia. In another embodiment, the route of administration may be directed to a different organ or system than the one that is affected by dermatologic conditions such as alopecia. For example, compounds may be administered parenterally to treat dermatologic conditions such as alopecia. Thus, the present invention provides for the use of FGF9 or other composition for use in the present invention in various dosage forms suitable for administration using any of the routes listed hereinabove.

In one embodiment, the methods of the present invention of testing a compound are repeated using a plurality of subjects, until a statistically significant sample has been tested.

In one embodiment, FGF9 augments hair germ formation in embryonic tissue, but is not essential for hair germ formation. In one embodiment, FGF9 is necessary for hair follicle formation and/or size in adult tissue after epidermal disruption.

In one embodiment, the signaling pathway for embryonic hair germ formation and for wound-induced hair follicle neogenesis share one or more components. In another embodiment, the signaling pathway for embryonic hair germ formation and for wound-induced hair follicle neogenesis is not identical. Thus, in one embodiment, FGF9 is essential for hair follicle to formation in WIHF but not during ED13.5.

In another embodiment, the signaling pathway for hair growth signals differs in different parts of the body. Thus, in one embodiment, embryonic hair germ formation and wound-induced hair follicle neogenesis differ in their dependence on FGF9 due to the differences in their respective developmental stages and differences in location in the body.

In one embodiment, the combination of FGF9 and wound healing increases its efficacy as a hair growth promoter. In one embodiment, FGF9 application alone causes epidermal thickening.

In another embodiment, the invention provides a method of treating hair loss or regenerating hair follicles in a subject comprising the step of disrupting the epidermis in the region of said hair loss in said subject. In some embodiments, the method further comprises the step of recruiting the gamma-delta T cells to the wound epidermis. In an exemplary embodiment, the method further comprises the step of recruiting the gamma-delta T cells to the wound epidermis through cytokines.

EXAMPLES

Experimental Details

Depilation and Epidermal Abrasion

Mice were anesthetized with an injection of sodium pentobarbital before the hair on the back was clipped and depilated with Nair (Carter-Wallace, New York, N.Y.), then epidermis was removed using a rotating felt wheel as described by Argyris T, J Invest Dermatol, 75: 360-362, 1980). After scrubbing with 70% ethanol and drying under an incandescent lamp, the basal and supra-basal layers in an area of $(1.5 \text{ cm})^2$ cm of the inter-follicular epidermis were removed by careful abrasion with a felt wheel mounted on a Dremel Moto-tool (Racine, Wis.). After abrasion, the skin was shiny and smooth, and there was no blood. One day later, the abraded area was covered by a fibrin crust, which fell off after 3-7 days, exposing the newly regenerated epidermis. A group of control mice was sacrificed immediately after abrasion to confirm microscopically the complete removal of the inter-follicular epidermis.

Punch Wound and Excisional Wound Induction

The backs of 21-day-old mice were depilated as described for Example 1 and sterilized with alcohol, followed by 1% iodine solution. Punch wounds, 4 mm in diameter, were induced using a dermal biopsy punch, down to, but not through, the muscle fascia. Excisional wounds were full thickness and 1 cm in diameter; skin and panniculus carnosus was excised using fine surgical scissors.

Immunohistochemistry

Skin samples were fixed in PBS-buffered 10% formalin. Six-micron thick paraffin sections were cut and stained, where applicable, with antibodies.

Whole Mounting and Immunofluorescence

HF whole mounts were obtained by incubating fresh skin with EDTA (20 mM in PBS) at 37° C. overnight, then separating the epidermis and dermis. Epidermis was then fixed in 10% formalin for 10 min, room temperature (RT). Dermis was fixed in acetone overnight, RT. After rinsing with PBS, whole mounts were stained with antibodies for immunohistochemistry (schematically depicted in FIG. 12) and were imaged using a Leica confocal microscope.

Statistics

Hair follicle numbers are expressed as mean±s.d. The student's two-tailed t-test function in Excel was used to calculate P values.

Embryonic Mouse Skin Culture Protocol

The following materials were used: Center well dishes (Fisher 08-772-12); Metal grids (Goodfellow 688-485-21); Nitrocellulose filters (Millipore AABP04700); Media: DMEM+5% FBS+1×Pen/Strep.

Gestational day 13.5 timed pregnant mothers (Charles River) were ordered. Center well dishes were set up with 2 ml media/dish. Metal grid was placed in center well. Dishes were stored in incubator so the media warmed to 37° C. Nitrocellulose filter were cut into rectangles and placed in a beaker of $dH_2O$ on a hot plate. Water was allowed to boil and then filters were boiled for 10 min.

Two petri dishes with sterile PBS were prepared. Mothers were euthanized and embryos were dissected out in the sac. Embryos were placed into one petri dish. The embryos were dissected out of the sac and placed in a second clean petri dish with sterile PBS. The dish of embryos were placed on ice. Dorsal skin was dissected from the embryo under a dissecting scope, in a clean petri dish containing sterile PBS.

The crown-rump length of the embryo was checked with a ruler to ensure it is E13.5 stage. (~10-10.3 mm). The head of the embryo was removed with micro dissecting scissors. A smaller pair of micro dissecting scissors were used to make incisions along both sides of the back, above the limbs. A third incision was made across the back, anterior to the tail. Using fine tipped Dumont tweezers, the skin was peeled from the tail towards the head. The skin was laid onto the black side of nitrocellulose filter, as flat as possible. The nitrocellulose filter was placed onto metal grid so that the skin is at the liquid-air interface. The dish was incubated at 37° C. When all skins were dissected, compounds were added to culture media (if necessary), and returned to the incubator. Skins were cultured for up to 3 days. Placodes started to develop on E14.5.

Example 1

FGF9 Expressed in Early Period Of Hair Germ Formation

Figure 2:
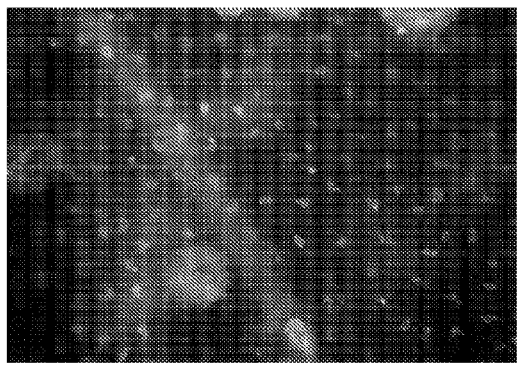
FIG. 2. γδTCR immunostaining of regenerated epidermis (SD7, wholemount) (×200) and FGF9 immunostaining of SD1 sample (frozen section) (×400).
Figure 2:
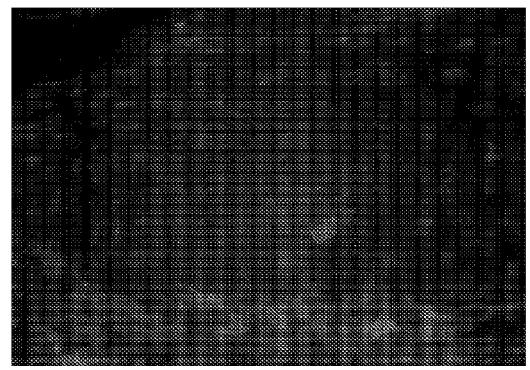
Figure 3:
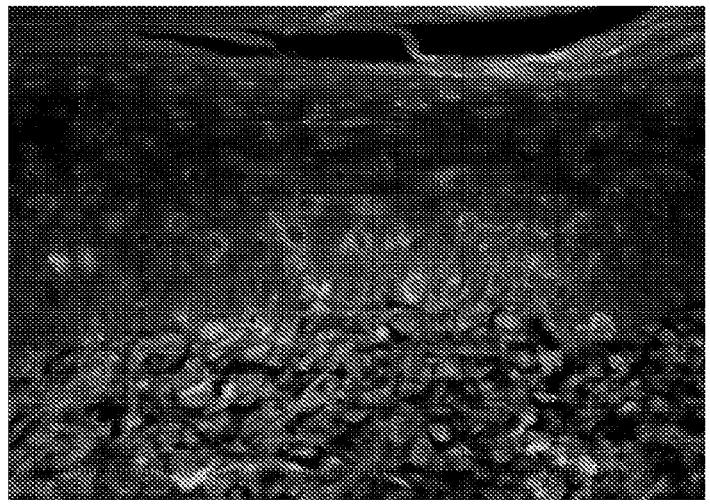
FIG. 3. γδTCR & FGF9 immunostaining of regenerated epidermis for SD1 sample.
Figure 3:
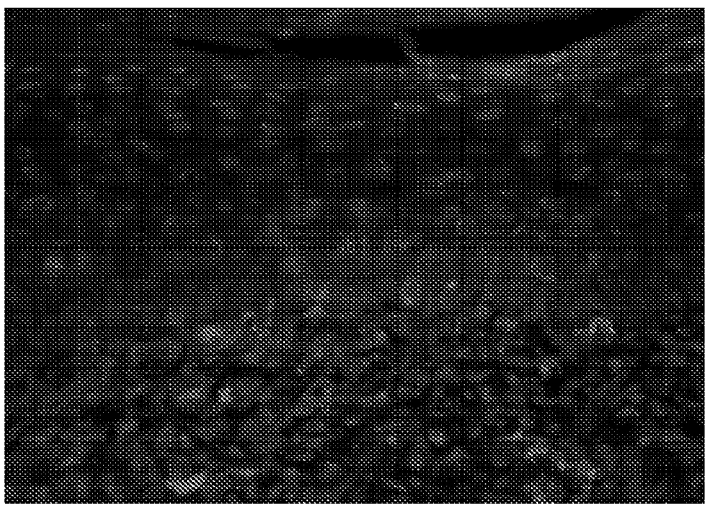
Figure 3:
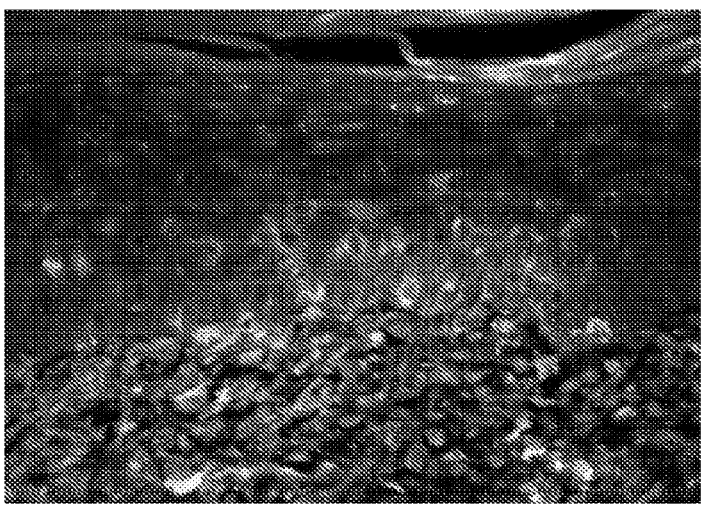

FGF9 mRNA expression was evaluated in regenerated epidermis by quantitative real time-PCR. FGF9 was expressed at higher levels prior to the earliest stages of hair follicle regeneration at Day 1 after scab detachment (SD; which occurs at reepithelialization) compared to Day 5 after scab detachment when follicles have formed (FIG. 1). Skin γδT-cells (detected by immunostaining using antibodies against γδTCreceptor) repopulate the reepithelialized epidermis by SD7 (FIG. 2, left panel) and these cells express FGF9 protein at SD1 (red dendritic cell in epidermis, FIG. 2, right panel, and FIG. 3).

Thus, FGF9 was selectively expressed prior to hair germ formation (during the undifferentiated period) rather than during differentiation. Skin γδT cells appeared to be the source of FGF9, which suggests inflammatory cells may have a role in Wound-induced hair follicle neogenesis (WIHN).

Example 2

FGF9 Expressed in Embryonic Day 14 (E14) Skin

Figure 4:
FIG. 4. γδTCR & FGF9 immunostaining of E14 embryonic skin.
Figure 4:
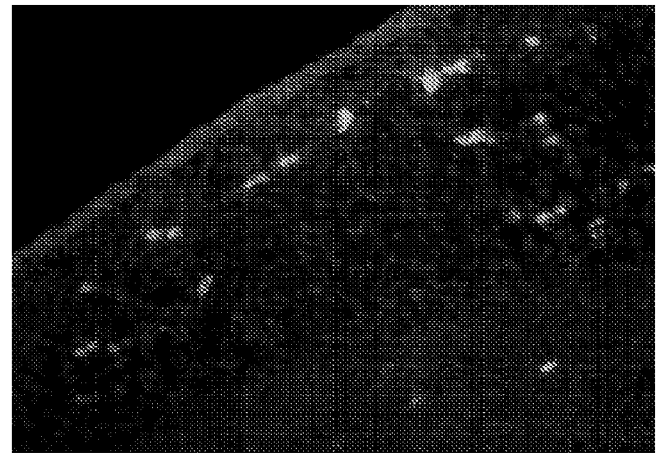
Figure 4:
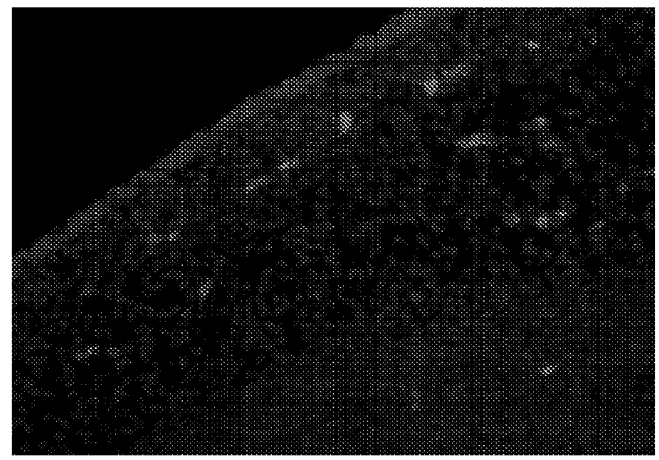
Figure 4:
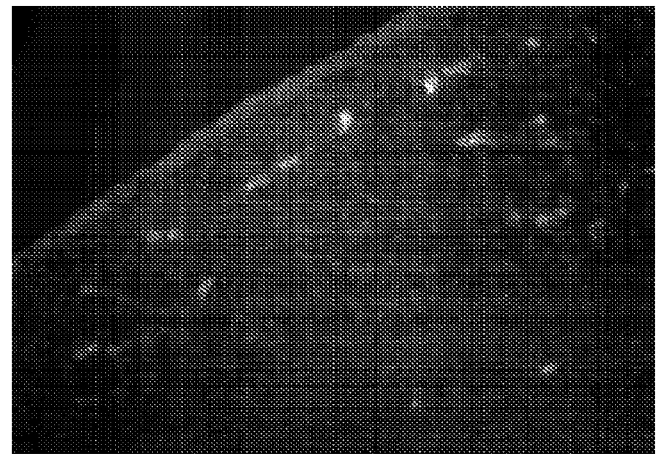

FGF9 (red staining) is expressed by γδTC (green staining) in embryonic day 14 (E14) skin (FIG. 4).

Example 3

FGF9 Plays a Role in Wound-Induced Hair Follicle Neogenesis (WIHN)

Anti-FGF9 Neutralization Experiment in Adult Mice 3 week-old (adult) C57BL/6 mice were subjected to the wounding model as described hereinabove. Mice then received subepidermal injections of 50 µl of 10 µg/ml anti-FGF9 or IgG2a isotype control on days SD1-SD4. Tissue samples were taken and analyzed at SD5.

Figure 5:
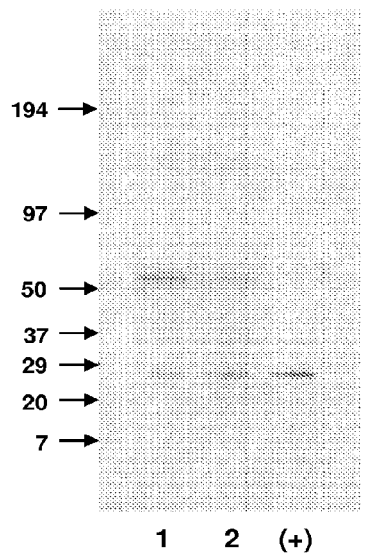
FIG. 5. Specificity of anti-FGF9 neutralization antibody for E14.5 mouse embryonal whole lysate (lanes 1 and 2) and for recombinant hFGF9 (+).

Immunoblots were used to verify the specificity of the anti-FGF9 neutralization antibody. Mouse FGF9 has 198 bp and greater than 99% homology with human FGF9 (with only one amino acid difference). FGF9 exists in both monomer (25-27 kd) and dimer forms. Immunoblots demonstrated the presence of both the 26 Kd monomer and the 52 Kd dimmer forms in E14.5 mouse embryonal whole cell lysates, as well as in control samples containing recombinant hFGF9 (FIG. 5).

Figure 6:
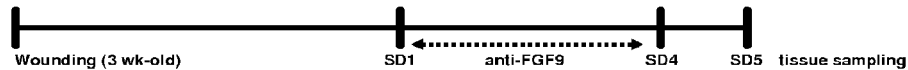
FIG. 6. Anti-FGF9 neutralization experiment in 3 week-old C57BL/6 mice. (A) Treatment schedule in which 50 μl of 10 μg/ml anti-FGF9 or IgG2a isotype control were injected subepidermally on scab detachment day (SD)1-SD4, and tissue was sampled at SD5. (B) Hair follicle numbers after anti-FGF9 or IgG2a control injections in mice using the treatment protocol described in (A). (C) Diagram showing injection site.
Figure 6:
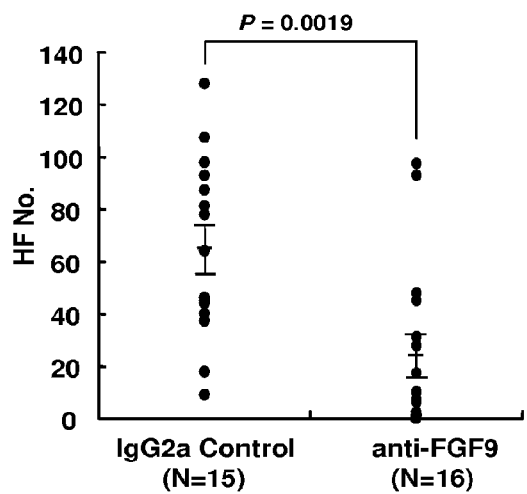
Figure 6:
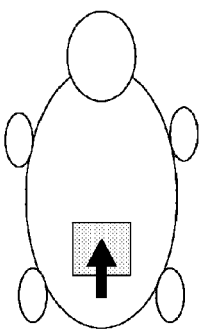

Mice receiving anti-FGF9 antibody had significantly lower hair follicle numbers on SD5 than IgG2a controls (FIG. 6). Thus, FGF9 plays a role in wound-induced hair follicle neogenesis.

Figure 7:
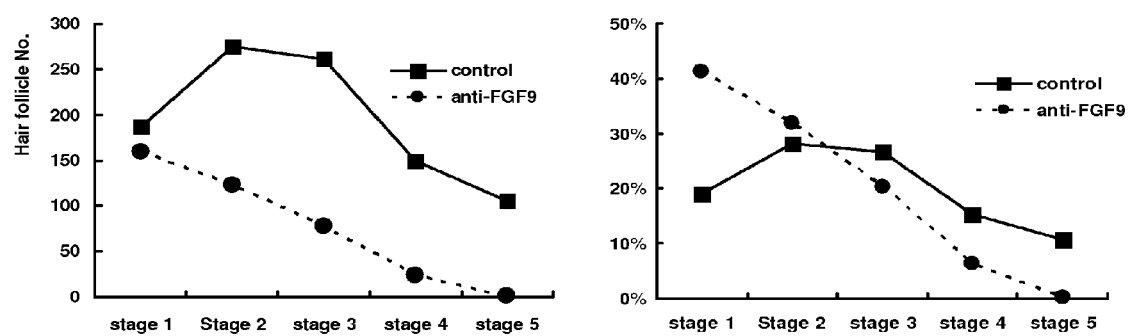
FIG. 7. Hair follicle number in anti-FGF9-treated mice vs controls at various stages of hair follicle development, as described in Paus R, et al. J Invest Dermatol 1999).

The developmental stages of the hair follicles were quantitated as described in Paus R et al., J Invest Dermatol 1999. There was a decrease in mature hair follicles and an increase in immature hair follicles in the anti-FGF9 treated group (FIG. 7).

Example 4

FGF9 Plays a Role in Embryonic Skin Development

Scheduled pregnant C57BL/6 mice were sacrificed at E13.5, and embryonic whole back skin was dissected. E13.5 skin was cultured for three days floated on filter paper with metal grid.

Figure 12:
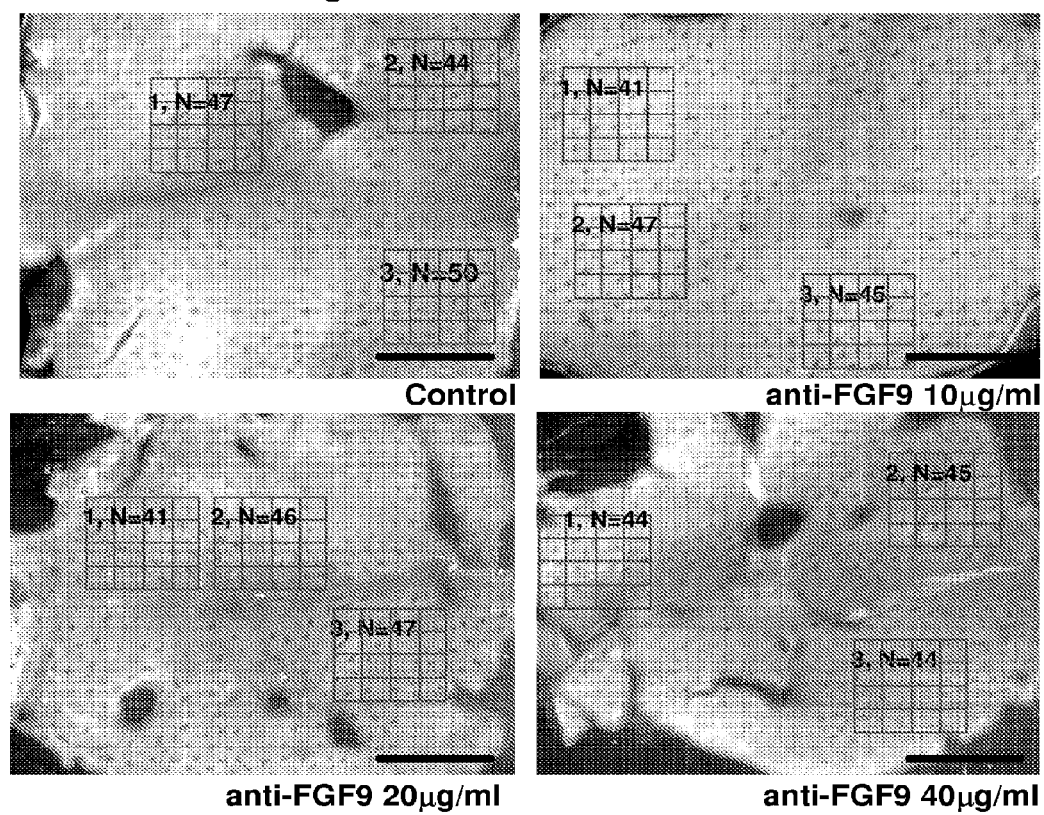
FIG. 12 Immunohistochemical staining showing K17 staining of the epidermis in control and anti-FGF9 (10, 20, 40 μg/ml)-treated skin explants.

To determine the role of FGF-9 in hair follicle neogenesis in embryonic skin, embryonic skin explant cultures were treated for three days with recombinant human (rh)FGF9 (control, 10, 20, or 40 ng/mL) or with an anti-FGF9 neutralizing antibody (control, 10, 20, or 40 µg/mL) or IgG2a isotype control (10, 20, 40 µg/mL). Alkaline phosphatase (AP) for dermis immunostaining (FIG. 10) and K17 was used for epidermis immunostaining (FIG. 12).

Figure 8:
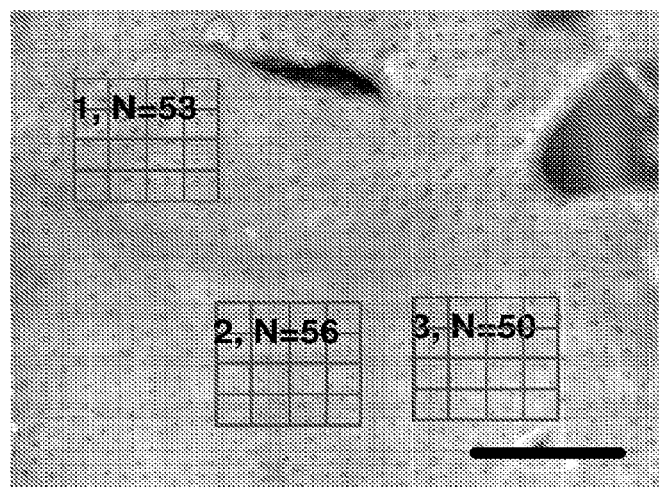
FIG. 8. Model showing how hair germ counting was conducted per $mm^2$ at 3 different fields per each sample.

Hair germ counting was performed at three separate fields per sample and was evaluated per $mm^2$ (FIG. 8). q-PCR for Shh, Ptch1, Ptch2, Gli1, and Gli2 was performed after 24 h of rhFGF9 treatment.

Real-Time PCR Protocol

The following materials were used: RNeasy® fibrous tissue mini kit (Qiagen, 74704); High capacity cDNA reverse transcription kit (Applied Biosystems, P/N 4368814); Taqman® Fast universal PCR master mix (2×) (Applied Biosystems, P/N 4352042); Applied Biosystems StepOne™ real-time PCR system; (Applied Biosystems, P/N 4376373);

MicroAmp™ 48-well optical adhesive film (Applied Biosystems, P/N 4375928); MicroAmp™ 48-well reaction plate (Applied Biosystems, P/N 4375816).

The following PCR primers were used (Taqman gene expression assay, Applied Biosystems):

TABLE 1

| Target gene | Gene name | Assay primer ID | Reference sequence |
|---|---|---|---|
| Fgf9 | fibroblast growth factor 9 | Mm00442795_m1 | NM_013518.3 |
| Shh | Sonic hedgehog | Mm00436527_m1 | NM_009170.3 |
| Ptch1 | patched homolog 1 | Mm00436026_m1 | NM_008957.2 |
| Ptch2 | patched homolog 2 | Mm00436047_m1 | NM_008958.2 |
| Gli1 | GLI-Kruppel family member GLI1 | Mm00494645_m1 | NM_010296.2 |
| Gli2 | GLI-Kruppel family member GLI2 | Mm01293116_m1 | NM_001081125.1 |
| ACTB (endogenous control) | actin, beta | P/N 4352933E | NM_007393.1 |

Protocol for q-PCR with Cultured Embryonic Skin Samples

Embryonic skin culture: E13.5 timed pregnant B57BL/6 female mice (Charles-River) were euthanized in $CO_2$ chamber. Embryos were dissected and placed in sterile cold PBS on ice.

Preparation: Millipore nitrocellulose membrane (0.5×1.0 cm2); Autoclave metal grids; Culture dishes (Falcon center-well organ culture dish, 35-3037); 5% FBS-DMEM (1× penicillin/streptomycin, not necessary to inactivate FBS).

2.5 mL of culture media was added and metal mesh and nitrocellulose membrane were set on the individual culture dishes. Embryonic back skin was dissected. Head & buttock area were cut. Dissection was through flank in a caudo-cranial direction. Dissected back skin was loaded on Millipore membrane (dermal side down). The samples were prepared in triplicate per needed for each concentration. Skin samples were cultured for 24 hr at 37° C. in 5% $CO_2$. RNA Isolation & cDNA Preparation Skin samples were incubated in 20 mM EDTA for 10 min Epidermis and dermis were separated with fine-tipped tweezers under a dissecting microscope, respectively.

Samples were disrupted with a homogenizer and total RNA extracted with RNeasy® fibrous tissue mini kit (Qiagen, 74704) following manufacturer's information.

RNA concentration was measured by spectrophotometer and then converted to lag of total RNA to cDNA using High capacity cDNA reverse transcription kit (Applied Biosystems, P/N 4368814) with program in thermal cycler.
Real-Time PCR PCR running program was set up and arranged the reaction plate layout with provided StepOne software in comparative CT (ΔΔCT) method. The reaction mixture of target gene and β-actin endogenous control were prepared together in triplicate. cDNA template was diluted from stock to final total cDNA amount of 30-50 ng in 24
Reaction Mix Components

| Component | Volume (μl) for 1 reaction |
|---|---|
| Taqman ® Fast universal PCR master mix (2X) | 10.0 |
| PCR primers (Taqman ® gene expression assay) | 1.0 |

-continued

| Component | Volume (μl) for 1 reaction |
|---|---|
| H2O | 7.0 |
| cDNA template | 2.0 |
| Total volume | 20.0 |

2. Prepare the reaction plate: A reaction volume of 20 μl/well is added on 48-well reaction plate. The plate is sealed tightly with optical adhesive film.

3. Load the plate into StepOne instrument and start the programmed reaction.

4. Analyze the results with the StepOne software and obtain relative quantitation data of gene expression.

Figure 9:
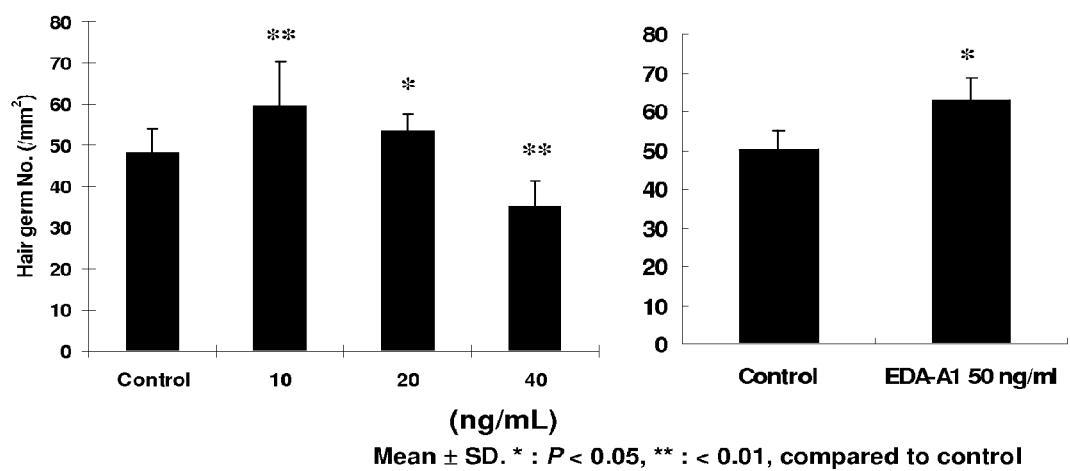
FIG. 9. rhFGF9 treatment for three days in embryonic skin explant culture (E13.5). Cultures were treated with 10, 20, or 40 ng/mL of rhFGF9 or control buffer for three days, and hair germ number/$mm^2$ was evaluated as described in FIG. 8. Mean±SD. *: P<0.05, **: P<0.01, compared to control. EDA-A1 (50 ng/ml) was used as a positive control for hair germ number.
Figure 10:
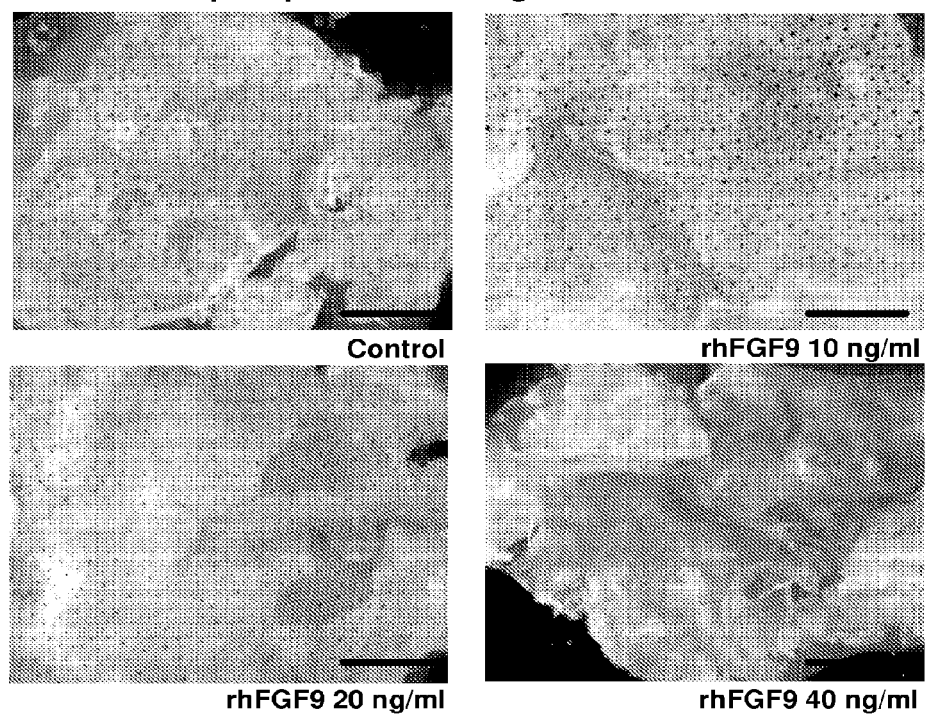
FIG. 10. Immunohistochemical staining showing alkaline phosphatase staining of the dermis in control and rhFGF9 (10, 20, 40 ng/ml)-treated embryonic skin explants.
Figure 11:
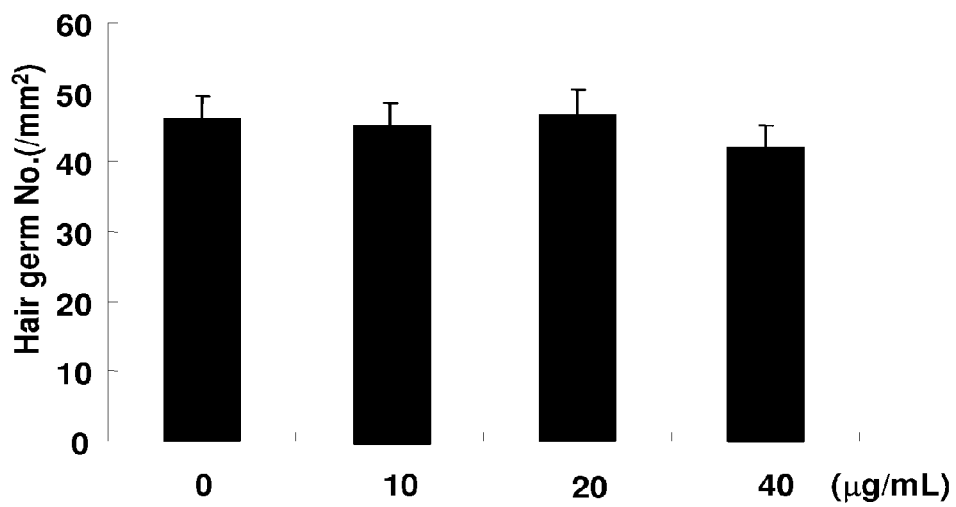
FIG. 11. Anti-FGF9 neutralizing antibody treatment for three days in embryonic skin explant culture (E13.5). Cultures were treated with 10, 20, or 40 μg/mL of anti-FGF9 neutralizing antibody or control for three days, and hair germ number/$mm^2$ was evaluated as described in FIG. 8.
Figure 13:
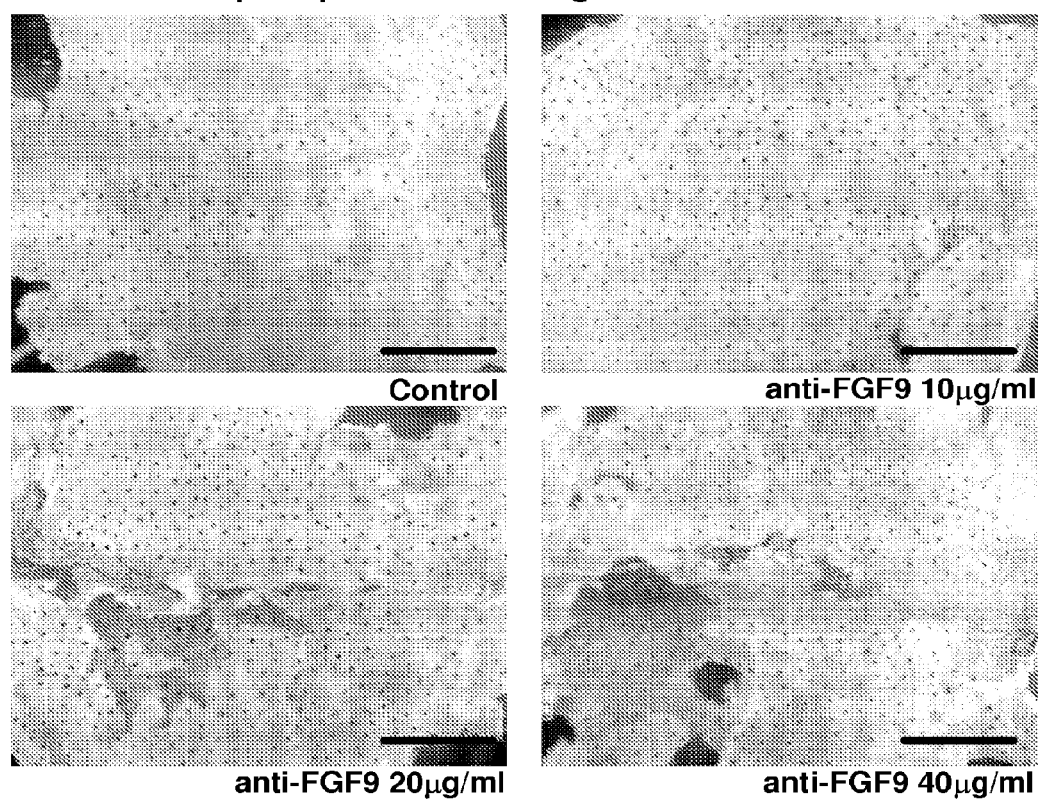
FIG. 13. Immunohistochemical staining showing alkaline phosphatase staining of the dermis in control and anti-FGF9 (10, 20, 40 μg/ml)-treated embryonic skin explants.

The effect of rhFGF9 treatment for three days in the dermis of embryonic skin explant culture (E13.5) was dose-dependent, with 10 ng/mL and 20 ng/ml resulting in an increase in hair germ number/$mm^2$, while a 40 ng/mL dose resulted in decreased hair germ number/$mm^2$ (FIGS. 9-10). On the other hand, there was no discernable effect of anti-FGF9 neutralizing antibody treatment for three days in the epidermis or dermis of embryonic skin explant culture (E13.5; FIGS. 11-13).

Figure 15:
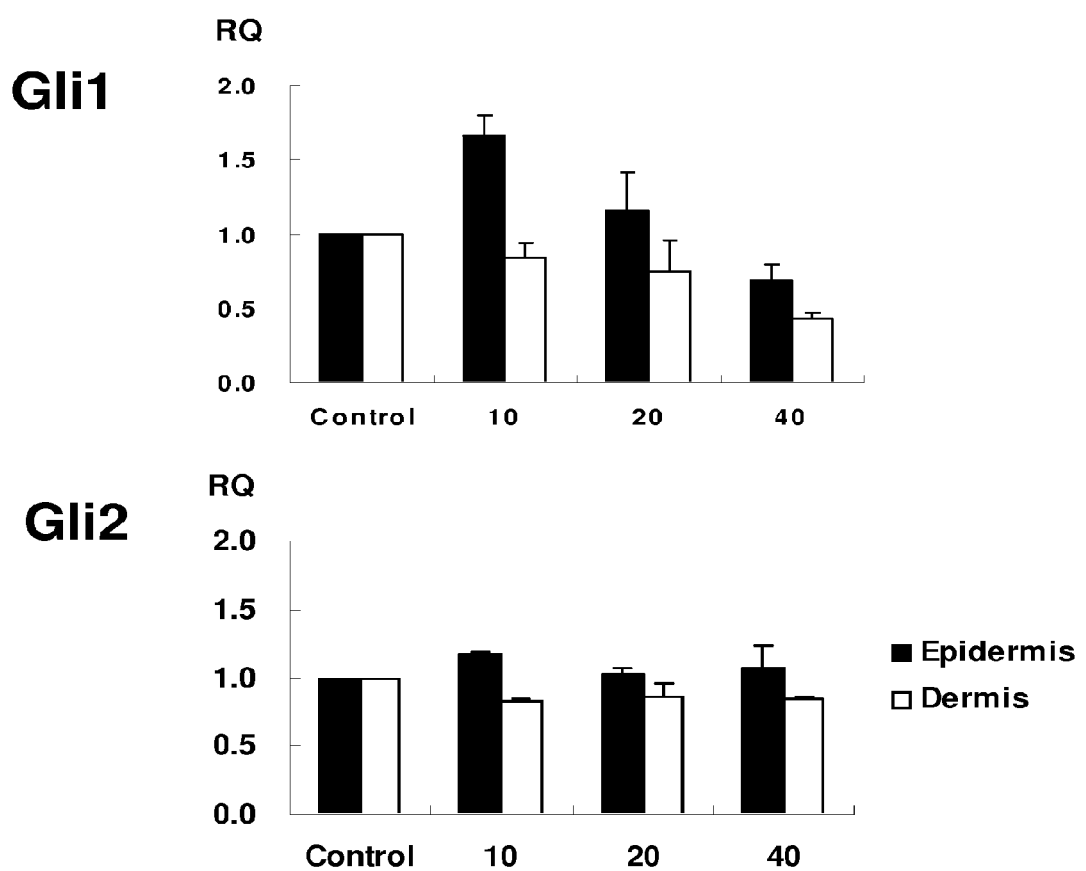
FIG. 15. Effect of 24 h treatment using rhFGF9 (10, 20, 40 ng/ml) on markers of embryonic hair follicle development Gli1 and Gli2 by qPCR.

24-hr treatment of E13.5 embryonic skin explant culture with 10 ng/mL of rhFGF9 resulted in increases in markers of embryonic hair follicle development including sonic hedgehog (Shh), Ptch1, Ptch2, and Gli1, particularly in the epidermis (FIGS. 14-15).

Fibroblast growth factor 9 increases hair follicle formation when injected into the wound after healing. This is just prior to and during the time when new hair follicles are forming FGF9 also increases hair follicle formation during hair follicle development by using embryonic mouse skin explanted in culture. These findings support the notion that wounding converts the epidermis to a "receptive" state in which it responds to exogenous factors.

Example 5

Overexpression of FGF9 in Basal Keratinocytes

The gain of function mutant TRE-fgf9-IRES-eGfp; K5-rtTA (xPtch1-LacZ reporter) (White et al., Development 133, 1507-1517, 2006; Diamond, et al. (2000) J. Invest. Dermatol. 115, 788-794, both incorporated herein by reference) is used to validate that early FGF9 expression in hair neogenesis stage would enhance hair follicle development and to confirm that FGF9 is upstream of Shh signaling.

Example 6

Deletion of FGF9 Expression in γδT Cells

Deletion of FGF9 expression in γδT cells is accomplished using the loss of function mutant FGF9flox/flox; lck-cre to selectively delete FGF9 using T-cell targeting lck-cre promoter. The Lck-Cre uses the proximal promoter of the Lck (lymphocyte protein tyrosine kinase) gene, which is first expressed early in thymocyte development at the double negative stage. After T cells fully mature, the level of expression of this transgene decreases by approximately 10 fold. This particular mouse gene shows a high degree of expression of the transgene in the thymus and has been found to bring about the selective deletion of genes flanked by loxP targeting sequences in almost all early thymocytes. It thus is used to delete a specific gene in the T cell lineage starting at the double negative stage. Since the homozygous Lck-Cre mice strains are crossed to a strain containing a floxed FGF9 and offspring with deleted FGF9 in the T cell lineage are obtained. Control animals are obtained in the same litter by typing for the presence or absence of the floxed gene in genomic DNA tail samples. This system is described in more detail in Lee et al., Immunity November 2001:15(5) 763-74, which is incorporated herein by reference.

Example 7

K17-EGFP Reporter Mice

K17-eGFP reporter mice (Bianchi et al., Mol Cell Biol., 2005 August; 25(16): 7249-7259, incorporated herein by reference) are used to confirm the accumulation of FGF9-producing γδT-cells around newly developing hair germs.

Example 8

FGF9 Mediates Hair Follicle Neogenesis Through Epidermal γδT CELLS

Understanding molecular mechanisms responsible for hair follicle regeneration during wound healing raises the opportunity to develop new treatments for hair loss and other skin disorders. Here, it is clearly shown that Fibroblast Growth Factor 9 (Fgf9) modulates hair follicle formation following wounding of adult mice. Forced overexpression of Fgf9 in the newly formed wound epidermis results in a 2-3-fold increase in the number of neogenic hair follicles. Remarkably, during wound healing in normal mice, γδT cells, which reside in the epidermis, serve as the primary source for Fgf9. Specific deletion of the Fgf9 gene in T cells using Lck-Cre; floxed fgf9 transgenic mice results in a marked reduction of hair follicle neogenesis following wounding. Similarly, mice lacking γδT cells demonstrate severe impairment of follicular neogenesis. Overall, these findings explain the robustness of hair follicle regeneration in mouse compared to human and highlight the important relationship between the immune system and tissue regeneration.

Materials and Methods:

Mice and Wounding.

Full thickness excision (FTE) of skin was performed on the back of C57BL/6J mice (Jackson laboratory) under ketamine/zylazine anesthesia as previously described (1). Three-week-old mice were used for all experiments with a 1×1 cm$^2$ FTE, except as indicated. Timed pregnant C57BL/6 female mice of gestational day 13.5 (Charles River) were utilized for embryonic skin explant culture. K14-rtTA mice harboring the doxycycline-sensitive transactivator were mated to TRE-Fgf9-IRES-eGfpmice. Both K14-rtTA and K14rtTA/TRE-Fgf9 mice were fed Dox-containing food (Bio-SERV) for 4 days after complete reepithelization. Deletion of FGF9 expression in γδT cells was accomplished using Fgf9 flox/flox mated to lck-cre mice (Jackson Laboratory) with T-cell targeting proximal promoter of the lymphocyte protein tyrosine kinase (lck). γδT cell null mice (Tcre) were purchased from Jackson Laboratory. All animal protocols were approved by the University of Pennsylvania IACUC.

Whole-Mount Hair Follicle Neogenesis Assay.

Healed skin was taken at day 5 after reepithelization. Whole-mount hair follicle neogenesis assays for epidermal KRT17 immunostaining (1:5000, from P. Coulombe) and dermal NBT/BCIP incubation were performed to identify new hair germs and follicular dermal papillae in wound area as previously described.

Real-Time PCR.

Dorsal skins were as day 0 samples or the wounded skin at day 1, 3 and 5 after scab detachment after reepithelization (SD), respectively. The epidermis was separated from dermis by incubation with 4° C. dispase overnight or 20 mM EDTA for 30 mM at 37° C. RNA was isolated using RNeasy minikit (Qiagen) and then 1 μg of total RNA was converted to cDNA with a High capacity cDNA kit (Applied Biosystems). All primer sets including fgf9 of Taqman gene expression assay were purchased from Applied Biosystems. Reactions were performed in triplicate and relative expression levels were standardized using β-actin as an internal control. The results were analyzed using StepOne program.

Immunostaining.

Reepithelialized skin after wounding was placed either frozen in OCT (Tissue-Tek). Staining for FGF9 (1:200; R&D systems) and γδTCR (1:100; GL3, BD Bioscience) were performed on 8 μm frozen section. Immunohistochemisty with antibodies against BrdU (1:500; Harlan-Seralab) was done as previously described. For pulse-chase experiments, BrdU (Sigma) was administered 2 hr before sample preparation.

Isolation of DETCs and Activation of the Cells.

Epidermal cell suspension was prepared from C57BL/6 mice and was incubated overnight at 37° C. in complete DMEM containing 20 U/ml of recombinant mouse IL-2 (mIL-2) to allow surface receptor re-expression as described. DETCs were isolated by FACS sorting with PE-γδTCR (GL3, Abcam) and allophycocyanin-Thy1.2 (BD Bioscience) staining. The isolated DETCs were cultured in RPMI-1640 medium supplemented with 10% FCS, 25 mM HEPES, 100 U penicillin, 100 μg streptomycin, 2 mM glutamine, 100 μM nonessential amino acids, 1 mM sodium pyruvate, 50 μM 2-mercaptoethanol and 20 U/ml mIL-2. For cell stimulation, the cells were harvested for 4 h in the growth factor-free media excluding FCS and mIL-2 and then incubated in the media described above supplemented with anti-CD3ε (10 m/ml, eBioscience) at 37° C. for 4, 24 and 48 h. Stimulation was arrested by the addition of ice-cold PBS and samples were placed on ice. Supernatants were removed and cells were collected with lysis buffer. RNA isolation and subsequent cDNA generation were performed with Gene expression cells-to $C_T$ kit (Applied Biosystems).

Wholemount Epidermal γδT Cell Staining.

Ears were cut from 8-week old C57BL/6J mice and epidermal sheets were separated as previously described. Epidermal sheets were incubated overnight in the growth factor-free media described above or complete media with 20 U/ml mIL-2 at 37° C. Epidermis was then washed in PBS and fixed in ice-cold acetone for 20 mM at −20° C. Primary antibodies of FGF9 and γδTCR mentioned above were incubated overnight at 4° C. The following morning, sheets were incubated with secondary antibodies for 1 hr and mounted on silane-coated slides.

In Vitro Embryonic Skin Culture.

Embryos at E13.5 were dissected out of the sac and the crown-lump length was checked to ensure exact developmental age. Dorsal skin was dissected and then cultured for up to 3 days as previously described. Recombinant human FGF-9 (0-20 ng/ml, R&D systems) or EDA1 (50 ng/ml, R&D systems) as a positive control were added into culture media. In addition, FGF9 neutralization experiment was paralleled with anti-FGF9 antibody incubation (0-40 mg/ml; MAB273, R&D systems). Epidermal-dermal separations were performed by incubating skin samples in 20 mM EDTA at 37° C.

for 5 min Tissues were homogenized to isolated RNA or harvested for wholemount assay as described above. The number of hair follicles was counted per mm² at 3 different fields of each sample and the mean value was calculated.

Neutralization Experiment in Adult Mice.

Reepithelization of epidermis, indicated by scab detachment, was complete 10-12 days after FTE. One day after complete reepithelization, 50 µl of anti-FGF9 neutralization antibody or IgG isotype control (MAB 003) at 10 µg/ml were daily injected just beneath epidermis for 4 consecutive days. After then, tissues were harvested at day 5, epidermis and dermis were separated using 20 mM EDTA solution and processed for KRT17 immunostaining and detecting alkaline phosphatase activity, respectively. The number of regenerated hair follicles was characterized with respect to their density inside the epidermis. The developmental stages of the hair follicles were quantified as previously described.

In Vivo Confocal Microscopy.

To chase dynamic process of hair follicle neogenesis, the changes of newly formed hair follicle number was quantified using in vivo confocal microscope (Vivascope 1500, Lucid). Briefly, surrounding area of healed skin was clipped and adhesive window (Lucid) and ultrasonic transmission gel (Parker laboratory) were applied under ketamine/zylazine anesthesia. New hair follicles could be visualized and counted at the level beneath epidermal-dermal junction. The number was measured at day 2 after reepithelization and then every 3 days for 2 weeks.

Results

Figure 16:
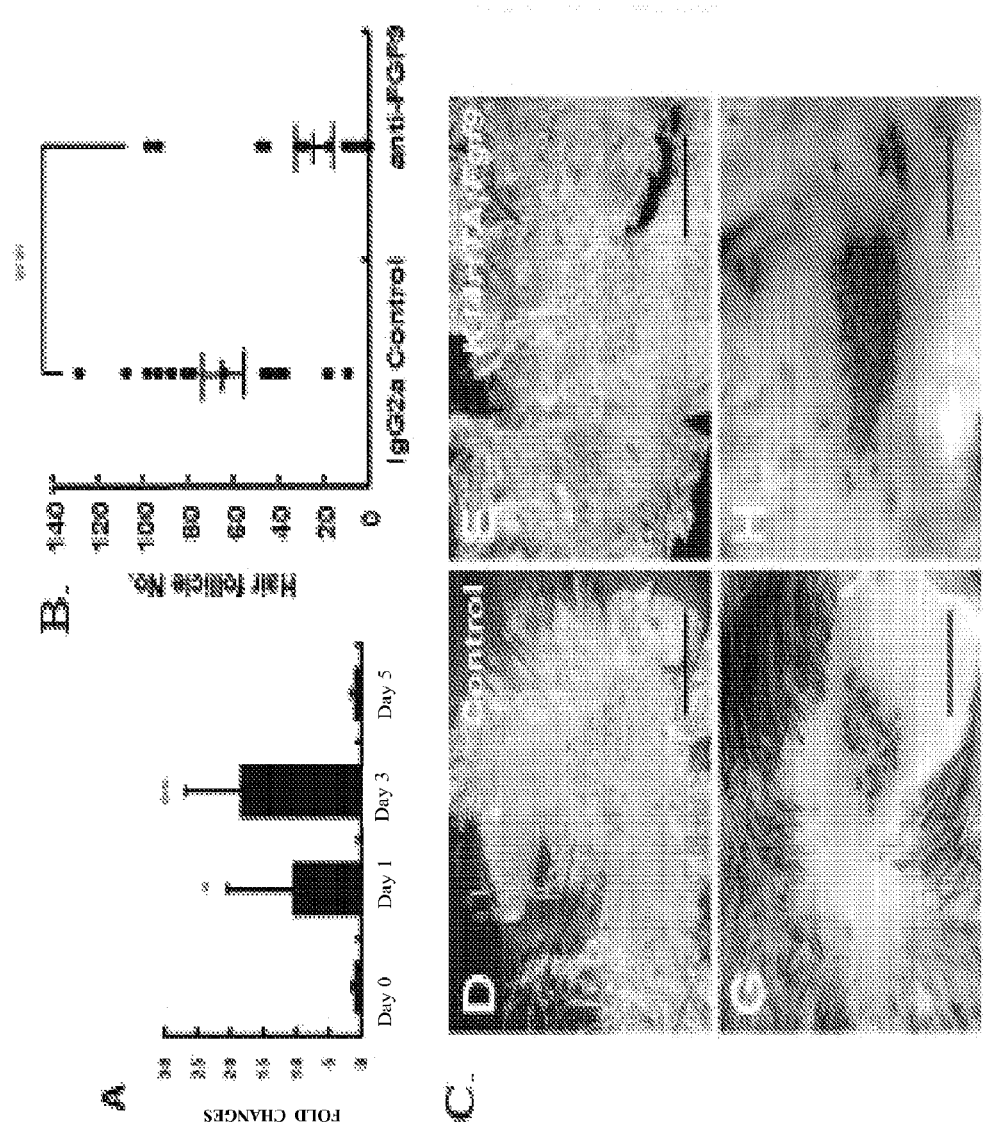
FIG. 16. Fgf9 is expressed during HFN initiation and is important to HFN. (A) Fgf9 is highly expressed in regenerated epidermis prior to hair follicle formation at Day 1 and 3 after reepithelization with scab detachment (SD) and decreased to basal level at Day 5. The ratio of Fgf9 mRNA expression in regenerated epidermis was compared to the level of unwounded epidermis, Day 0. *: P<0.05, : P<0.01, mean±standard deviation. (B) Effect of FGF9 neutralization on HFNafter wounding in 3-week old mice. The number of regenerated hair follicles was significantly decreased in the mice treated with anti-FGF9 neutralizing antibody compared to controls. : P<0.05 (B) Determination of developmental stages of hair follicles. Hair follicles in the anti-FGF9-treated mice showed delay in hair follicle maturation. (C-E) Wholemount hair follicle neogenesis assay stained for KRT17 protein and (F—H) alkaline phosphatase activity in separated epidermis and dermis at Day 5 after reepithelization, respectively. Overexpression of Fgf9 in K14rtTA;TRE-Fe-IRES-eGfp mice resulted in increased numbers of hair follicles at Day 17 after wounding. Scale bar, 1 mm.

Fgf9 Expression Significantly Increases after Wounding Prior to Hair Follicle Neogenesis:

To define molecular events responsible for hair follicle neogenesis following wounding, we compared gene expression in wounded epidermis soon after reepithelization (1 and 3 days after scab detachment "SD") to the initiation of hair follicle neogenesis (SD5). Microarray analyses showed that Fibroblast growth factor 9 (Fgf9) was significantly upregulated (4.2 fold) prior to hair follicle germ formation. We further analyzed Fgf9 gene expression changes in reepithelialized epidermis around the time of hair follicle neogenesis by quantitative RTPCR (FIG. 16A). Fgf9 gene expression increased significantly after reepithelialization until to the initial stages of hair follicle neogenesis when expression decreased dramatically. These results show that Fgf9 is upregulated in the newly formed epidermis just prior to hair follicle neogenesis presumably at a time when cells are committing to the hair follicle lineage.

Inhibition of Fgf9 Decreases Hair Follicle Neogenesis.

Figure 19:
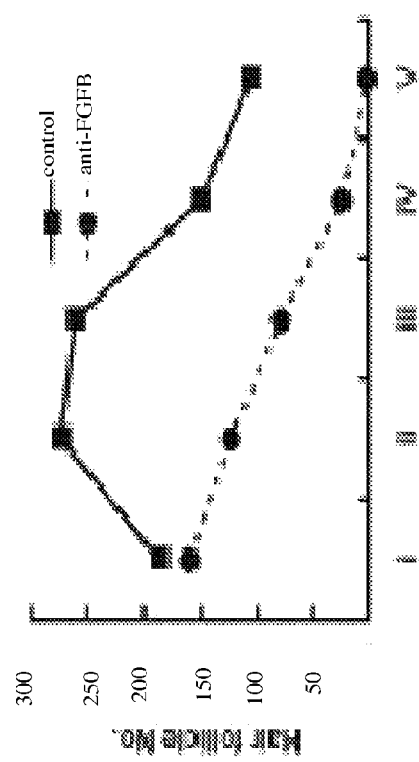
FIG. 19. Developmental stages of HFs in control and anti-fgf9 antibody-treated wounds.

Fgf9 is a secreted ligand with a known role in lung, kidney and gonad development, but it has not been previously implicated in hair follicle development or regeneration. Nevertheless, the main receptor for Fgf9 in the skin, Fgr3b, is expressed in epidermis and is upregulated in regenerated skin after wounding. To address the importance of Fgf9 in hair follicle neogenesis following wounding, we injected Fgf9 neutralizing antibody into the reepithelialized skin daily for four days (FIG. 16b, Table 2). Wounds treated with anti-Fgf9 antibody showed a significant reduction of new hair follicle formation when compared with controls. The hair follicles that did form in anti-Fgf9-treated wounds were in immature stages of development (FIG. 19).

Forced Overexpression of Fgf9 in the New Epidermis Increases Hair Follicle Formation.

Figure 20:
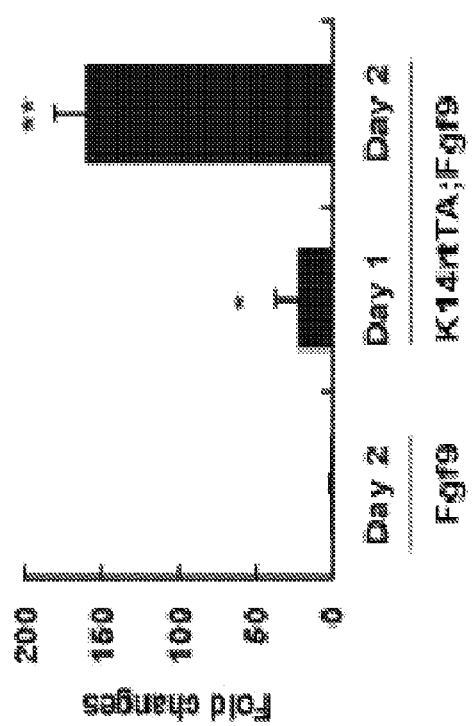
FIG. 20. FGF9 expression in K14rtTA;TRE-fgf9-IRES-eGfp mice compared to control mice during 2 days of doxycycline treatment.

Since blocking Fgf9 inhibited hair follicle neogenesis, we asked whether increasing levels of Fgf9 in the wound would promote hair follicle neogenesis following wounding. We used a doxycycline-inducible transgenic mouse (K14rtTAx TRE-Fgf9-IRES-eGfp) to inducibly target Fgf9 expression to the epidermis following wound re-epithelialization. Administration of doxycycline from SD1 to SD4 increased Fgf9 expression 150-fold (FIG. 20) compared to doxycycline treated control mice. This targeted overexpression of Fgf9 to the epidermis for four days after reepithelialization led to a marked increase in the number of hair follicles compared to controls (FIG. 16c, Table2).

TABLE 2

Hair follicle neogenesis assay.

| Experiment | mice | Hair follicle No. (mean ± SD) | Mice No. | Range | F-value |
|---|---|---|---|---|---|
| Deletion of FGF9 in T cells | lck-cre; Fgf9$^{flox/flox}$ | 9.1 ± 16.7 | 11 | 0-49 | <0.05 |
| | Fgf9$^{flox/flox}$, Fgf9$^{flox/+}$ (Control) | 30.7 ± 34.0 | 15 | 1-131 | |
| FGF9 overexpression | Double transgenic K14rtTA; TRE-Fgf9-IRES-eGfp | 168.2 ± 117.1 | 12 | 2-189 | <0.05 |
| | Single transgenic K14rtTA, TRE-Fgf9-IRES-eGfp (Control) | 64.8 ± 50.3 | 21 | 26-431 | |
| Absence of γδ T cells | 8-week old wild-type (1.5 × 1.5 cm² wounding) | 43.4 ± 31.7 | 8 | 1-87 | NS |
| | 24-40 week old wild-type (1.5 × 1.5 cm² wounding) | 36.7 ± 24.5 | 6 | 1-76 | |
| | 8-week old γδ T cell null mice (1.5 × 1.5 cm wounding) | 9.8 ± 10.1 | 13 | 0-27 | <0.01 |
| | 24-40 week old γδ T cell null mice (1.5 × 1.5 cm wounding) | 7.8 ± 13.7 | 8 | 0-39 | |

The number of new hair follicles were counted at Day 5 after reepithelization. NS: not significant.

Fgf9 Expression Localizes to γδT Cells.

Figure 17:
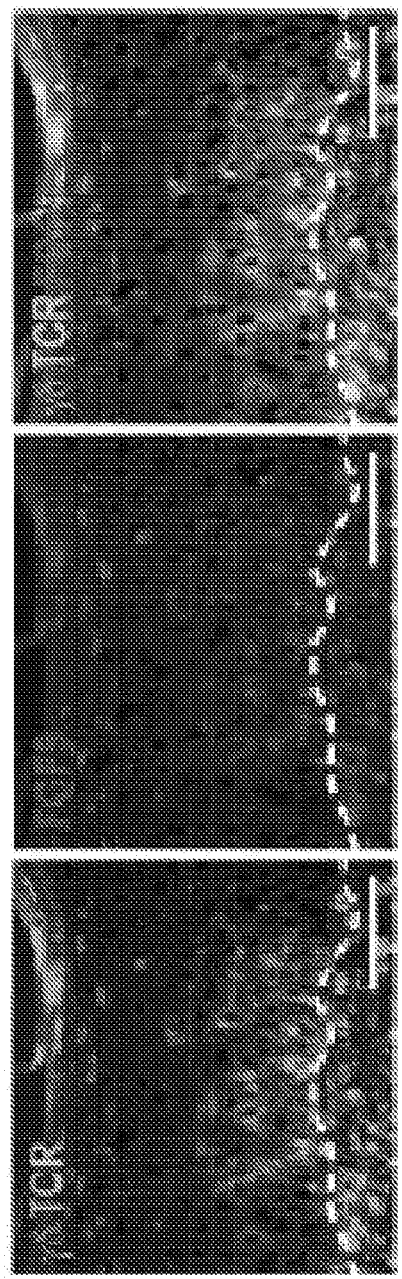
FIG. 17. FGF9 is expressed by activated DETC (A) Double immunostaining for FGF9 and γδTCR. Fgf9 expression in repopulated γδTCR-positive DETCs after reepithelization. Dot line, basement membrane. Scale bar, 50 μm. (B) Fgf9 gene expression is highly upregulated in the isolated DETCs after activation with mIL-2 and anti-CD3.
Figure 17:
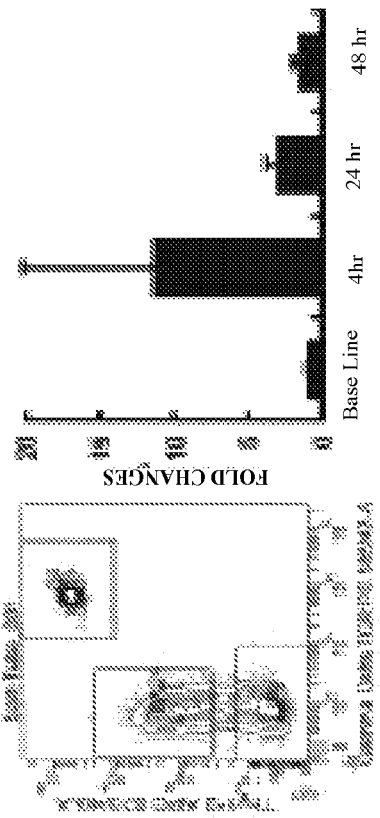
Figure 21:
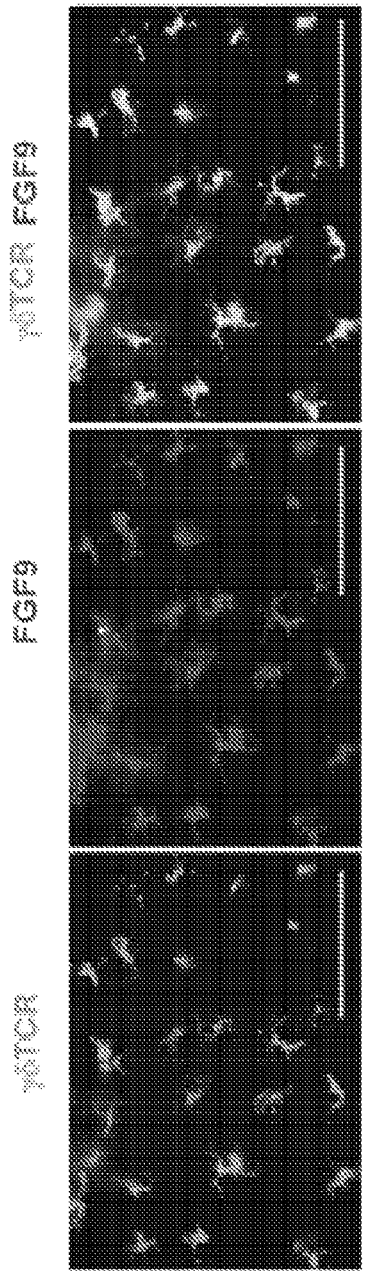
FIG. 21. FGF9 expression in DETCs. (A) FGF9 is highly expressed in suprabasal dendritic cell. Wholemount double immunostaining of FGF9 and γδTCR of ear epidermis from wild-type mouse without (B) or with IL-2 incubation (C).

To identify the source of Fgf9 in re-epithelialized skin of normal mice, we immunostained tissue sections of healed skin prior to HFN. Surprisingly, we discovered that γδT cell receptor-bearing epidermal T cells (DETC), which repopulate the epidermis, express Fgf9. DETCs appear to be the primary source of Fgf9 in epidermis, with little or no contribution from keratinocytes or other epithelial residents (FIG. 17A). Previous gene expression data from basal keratinocytes (Alpha-6-integrin-positive) isolated by FACS showed an absence of Fgf9 expression (NAT BIOTech paper). To further confirm the origin of the Fgf9, we treated unwounded ear epidermis with mIL-2 and analysed wholemount preparations for Fgf9 expression by immunofluorescence. IL2-induced DETCs stained strongly with anti-FGF9 antibodies whereas adjacent keratinocytes exhibited background staining (FIG. 21).

To determine if FGF9 is constitutively expressed by DETCs in skin or upregulated following stimulation, DETCs were isolated from skin by cell sorting and were cultured in vitro with anti-CD3 and IL2 as previously described (havren ref). Fgf9 mRNA levels increased by to greater than 10 fold within 4 hours, followed by diminution to baseline levels within 24 hours. (FIG. 17B). This rapid upregulation contrasts with the much longer 48 hour induction period required for expression of FGF7 and FGF10, two factors known to be secreted by DETCs during wound repair and indicates distinct transcriptional regulatory mechanisms.

DETCs are Essential for Hair Follicle Neogenesis.

Since Fgf9 mediates hair follicle neogenesis and DETCs appear to be the primary source of Fgf9 in re-epithelialized epidermis, we hypothesized that activated DETCs repopulate the wound during reepithelialization and secrete FGF9 to induce hair follicle neogenesis. To better define the role of DETCs in hair follicle neogenesis, we studied Tcrd−/− mice that fail to develop these cells.

We wounded age-matched wild-type and Tcrd−/− mice at 8 or 24-40 weeks of age and quantified hair follicle neogenesis. As previously reported, TCRd−/− mice showed slight delays in wound closure (data not shown), but hair follicle neogenesis was markedly decreased. Quantitation of Fgf9 levels indicated that Fgf9 was consistently negligible in the Tcrd−/− mice.

Figure 18:
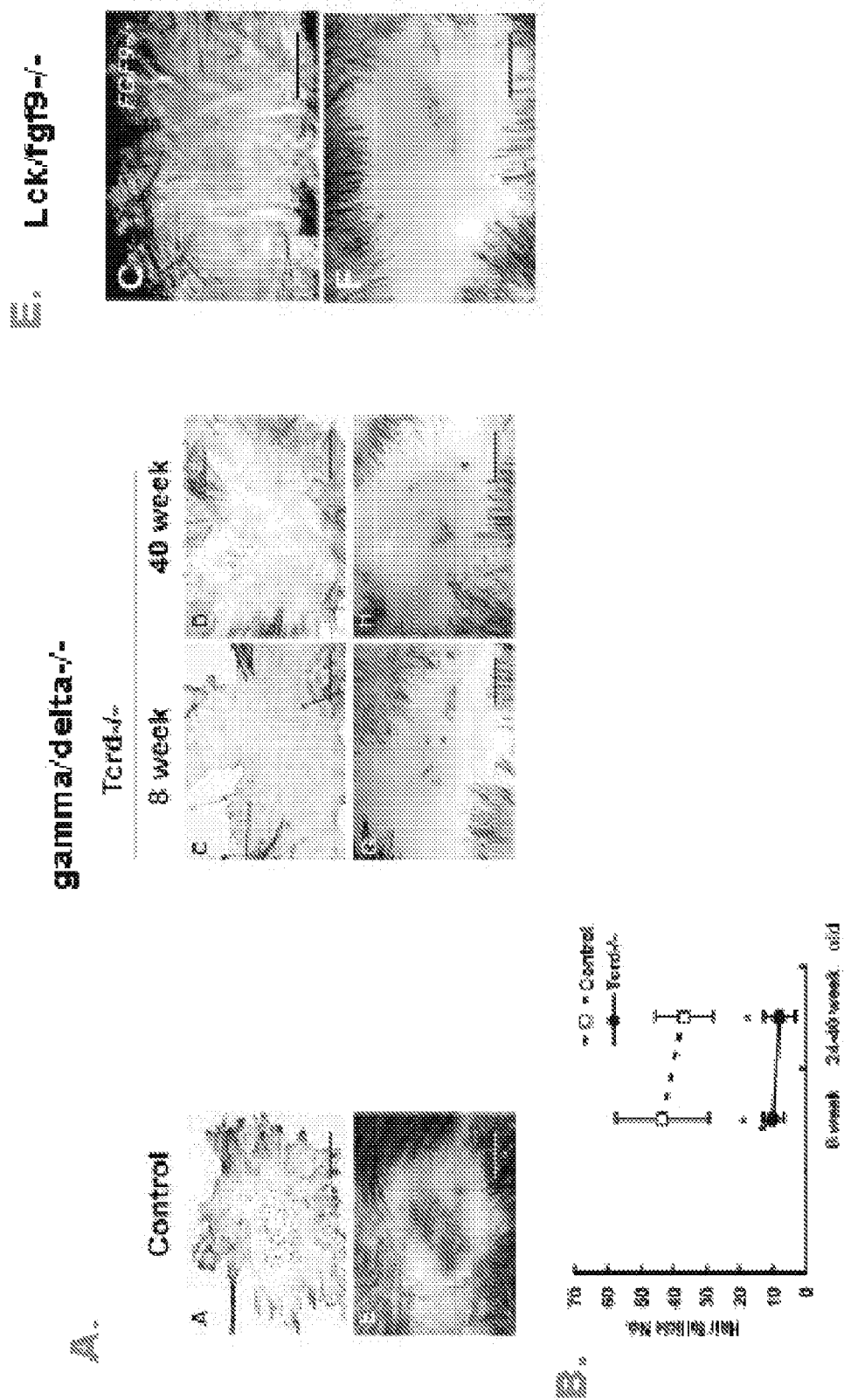
FIG. 18. Hair follicle neogenesis in TCRd−/− mice is severely impaired. (A-D) Wholemount epidermal and dermal samples treated to detect KRT17 protein and (E-H) alkaline phosphatase activity at Day 5 after reepithelization. Hair follicle formation was significantly impeded in 8 week and 40 week old mice. Scale bar, 1 mm *: P<0.05, mean±standard error.

As shown in FIG. 18, 8 wk and 40 wk−/− mice exhibited profound defects in HFN, with reductions of >80% in HF numbers compared with wt mice (18A,B, Table 2). Thus, reduced numbers of HFs in −/− mice reflect a true defect in hair follicle neogenesis rather than delayed kinetics of response.

Figure 22:
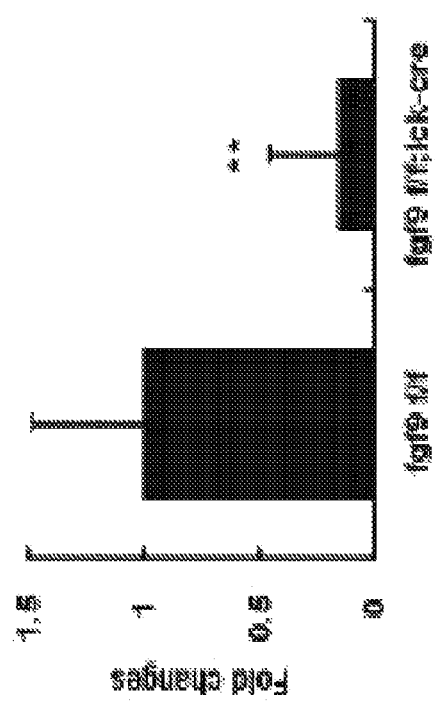
FIG. 22. FGF9 expression in FGF9$^{flox/flox}$; lck-cre mice compared to FGF9$^{flox/flox}$ control.

The above findings supported the hypothesis that activation of DETCs following wounding leads to FGF9 production and subsequent hair follicle neogenesis. Nevertheless, to address the concern that DETCs may have a role in hair follicle neogenesis other than the production of FGF9, mutant (lck-cre×Fgf9$^{flox/flox}$) mice carrying a deletion of the FGF9 gene specifically in T cells, including DETCs, were analysed for hair follicle neogenesis following wounding. Quantitative rtPCR analyses showed that these mice express low constitutive levels of FGF9 in skin. (FIG. 22). Wounding studies showed that these mutant (lck-cre×Fgf9$^{flox/flox}$) mice exhibited a dramatic reduction in post-wound hair follicle numbers comparable to that observed in TCRd−/− animals (FIG. 18E, Table 2).

Taken together, the above described results show that DETCs are essential immunologic contributors to HF neogenesis through the production of FGF9.

In summary, we discovered that DETCs are the source of FGF9. Further, the findings indicate that more divergent cellular & molecular events could be implicated in HFN after wounding, not exactly the recapitulation of embryonic development, and provide additional evidence that acquired immune system including DETCs would have a role in tissue regeneration.

FGF9 and DETCs are critical for HFN after wounding. Overexpression of FGF9 in reepithelized epidermis resulted in increase of hair follicle formation. These results show that manipulation of FGF9 expression during wound healing or after reepithelization could be a useful approach to develop a new treatment for hair loss.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of treating hair loss in a subject comprising the steps of (a) disrupting the epidermis in the region of said hair loss in said subject and (b) administering a composition comprising a fibroblast growth factor-9 polypeptide to said subject.

2. The method of claim 1, wherein said hair loss is due to androgenetic alopecia (AGA).

3. The method of claim 2, wherein said AGA is male pattern baldness.

4. The method of claim 2, wherein said AGA is female pattern baldness.

5. The method of claim 1, wherein said hair loss is the result of a skin injury.

6. The method of claim 1, wherein said hair loss is in the scalp or eyebrow of said subject.

7. The method of claim 1, wherein said hair loss is in scarred skin tissue of said subject.

8. The method of claim 1, wherein said step of administering is performed 3-12 days after said step of disrupting.

9. The method of claim 1, wherein said step of disrupting is performed by exposing the region of said hair loss to a mechanical or chemical stimulus.

10. The method of claim 1, wherein said step of disrupting is performed by exposing the region of said hair loss to radiation.

11. The method of claim 1, wherein said administering step is via topical administration.

12. The method of claim 1, wherein said administering step is via subepidermal administration.

13. A method for generating a hair follicle in the dermis of a subject with hair loss comprising the steps of (a) disrupting the epidermis in the region of said hair loss in said subject and (b) administering a composition comprising a fibroblast growth factor-9 polypeptide to said subject.

14. The method of claim 13, wherein said subject has a reduced number of hair follicles as a result of androgenetic alopecia (AGA).

15. The method of claim 14, wherein said AGA is male pattern baldness.

16. The method of claim 14, wherein said AGA is female pattern baldness.

17. The method of claim 13, wherein said subject has a reduced number of hair follicles as a result of a skin injury.

18. The method of claim 13, wherein said subject has a reduced number of hair follicles in the scalp or eyebrow, relative to a healthy normal scalp or eyebrow.

19. The method of claim 13, wherein said subject has a reduced number of hair follicles in scarred skin tissue, relative to a healthy unscarred skin tissue.

20. The method of claim 13, wherein said step of administering is performed 3-12 days after said step of disrupting.

21. The method of claim 13, wherein said step of disrupting is performed by exposing said region of hair loss to a mechanical or chemical stimulus.

22. The method of claim 13, wherein said step of disrupting is performed by exposing the region of said hair loss to radiation.

23. The method of claim 13, wherein said administering step is via topical administration.

24. The method of claim 13, wherein said administering step is via subepidermal administration.

25. A method for increasing the size of a hair follicle in the dermis of a subject with hair loss comprising the steps of (a) disrupting the epidermis in the region of said hair loss in said subject and (b) administering a composition comprising a fibroblast growth factor-9 polypeptide to said subject.

26. The method of claim 25, wherein said subject has reduced hair follicle size as a result of androgenetic alopecia (AGA).

27. The method of claim 26, wherein said AGA is male pattern baldness.

28. The method of claim 26, wherein said AGA is female pattern baldness.

29. The method of claim 25, wherein said subject has reduced hair follicle size as a result of a skin injury.

30. The method of claim 25, wherein said subject has reduced hair follicle size in the scalp or eyebrow, relative to a healthy normal scalp or eyebrow.

31. The method of claim 25, wherein said subject has reduced hair follicle size in scarred skin tissue, relative to a healthy unscarred skin tissue.

32. The method of claim 25, wherein said step of administering is performed 3-12 days after said step of disrupting.

33. The method of claim 25 wherein said step of disrupting is performed by exposing said region of hair loss to a mechanical or chemical stimulus.

34. The method of claim 25, wherein said step of disrupting is performed by exposing the region of said hair loss to radiation.

35. The method of claim 25, wherein said administering step is via topical administration.

36. The method of claim 25, wherein said administering step is via subepidermal administration.

37. A method for increasing hair follicle formation in the skin of a subject with hair loss comprising the steps of (a) disrupting the epidermis in the region of said hair loss in said subject and (b) administering a composition comprising a fibroblast growth factor-9 polypeptide to said subject.

38. The method of claim 37, wherein said subject has decreased hair follicle numbers as a result of androgenetic alopecia (AGA).

39. The method of claim 37, wherein said subject has decreased hair follicle numbers as a result of a skin injury.

40. The method of claim 37, wherein said step of administering is performed 3-12 days after said step of disrupting.

41. The method of claim 37, wherein said step of disrupting is performed by exposing a region of said dermis of said subject comprising low hair follicle numbers to a mechanical or chemical stimulus or to radiation.

42. The method of claim 37, wherein said administering step is via topical administration.

43. The method of claim 37, wherein said administering step is via subepidermal administration.

44. A method for treating an androgenetic alopecia (AGA) in a scalp of a subject comprising the steps of (a) disrupting the epidermis in the region of said AGA in said subject and (b) administering a composition comprising a fibroblast growth factor-9 polypeptide to said subject.

45. The method of claim 44, wherein said step of administering is performed 3-12 days after said step of disrupting.

46. The method of claim 44, wherein said step of disrupting is performed by exposing the region of said AGA to a mechanical or chemical stimulus or to radiation.

47. The method of claim 44, wherein said administering step is via topical administration.

48. The method of claim 44, wherein said administering step is via subepidermal administration.

49. A method of treating hair loss in a subject comprising the step administering a composition comprising a fibroblast growth factor-9 polypeptide and a wnt polypeptide to said subject.

50. The method of claim 49, wherein said wnt polypeptide is a wnt7 polypeptide.

51. The method of claim 49, wherein said hair loss is due to androgenetic alopecia (AGA).

52. The method of claim 51, wherein said AGA is male pattern baldness.

53. The method of claim 51, wherein said AGA is female pattern baldness.

54. The method of claim 49, wherein said hair loss is the result of a skin injury.

55. The method of claim 49, wherein said hair loss is in the scalp or eyebrow of said subject.

56. The method of claim 49, wherein said hair loss is in scarred skin tissue of said subject.

57. The method of claim 49, wherein said administering step is via topical administration.

58. The method of claim 49, wherein said administering step is via subepidermal administration.

59. A method for generating a hair follicle in the dermis of a subject comprising the step of administering a composition comprising a fibroblast growth factor-9 polypeptide and a wnt polypeptide to said subject.

60. The method of claim 59, wherein said wnt polypeptide is a wnt7 polypeptide.

61. The method of claim 59, wherein said subject has a reduced number of hair follicles as a result of androgenetic alopecia (AGA).

62. The method of claim 61, wherein said AGA is male pattern baldness.

63. The method of claim 61, wherein said AGA is female pattern baldness.

64. The method of claim 59, wherein said subject has a reduced number of hair follicles as a result of a skin injury.

65. The method of claim 59, wherein said subject has a reduced number of hair follicles in the scalp or eyebrow, relative to a healthy normal scalp or eyebrow.

66. The method of claim 59, wherein said subject has a reduced number of hair follicles in scarred skin tissue, relative to a healthy unscarred skin tissue.

67. The method of claim 59, wherein said administering step is via topical administration.

68. The method of claim 59, wherein said administering step is via subepidermal administration.

69. A method for increasing the size of a hair follicle in the dermis of a subject comprising the step of administering a composition comprising a fibroblast growth factor-9 polypeptide and a wnt polypeptide to said subject.

70. The method of claim 69, wherein said wnt polypeptide is a wnt7 polypeptide.

71. The method of claim 69, wherein said subject has reduced hair follicle size as a result of androgenetic alopecia (AGA).

72. The method of claim 71, wherein said AGA is male pattern baldness.

73. The method of claim 71, wherein said AGA is female pattern baldness.

74. The method of claim 69, wherein said subject has reduced hair follicle size as a result of a skin injury.

75. The method of claim 69, wherein said subject has reduced hair follicle size in the scalp or eyebrow, relative to a healthy normal scalp or eyebrow.

76. The method of claim 69, wherein said subject has reduced hair follicle size in scarred skin tissue, relative to a healthy unscarred skin tissue.

77. The method of claim 69, wherein said administering step is via topical administration.

78. The method of claim 69, wherein said administering step is via subepidermal administration.

79. A method for increasing hair follicle formation in the skin of a subject comprising the step of administering a composition comprising a fibroblast growth factor-9 polypeptide and a wnt polypeptide to said subject.

80. The method of claim 79, wherein said wnt polypeptide is a wnt7 polypeptide.

81. The method of claim 79, wherein said subject has decreased hair follicle numbers as a result of androgenetic alopecia (AGA).

82. The method of claim 79, wherein said subject has decreased hair follicle numbers as a result of a skin injury.

83. The method of claim 79, wherein said administering step is via topical administration.

84. The method of claim 79, wherein said administering step is via subepidermal administration.

85. A method for treating an androgenetic alopecia (AGA) in a scalp of a subject comprising the step of administering a composition comprising a fibroblast growth factor-9 polypeptide and a wnt polypeptide to said subject.

86. The method of claim 85, wherein said wnt polypeptide is a wnt7 polypeptide.

87. The method of claim 85, wherein said administering step is via topical administration.

88. The method of claim 85, wherein said administering step is via subepidermal administration.

\* \* \* \* \*

UNITED STATES PATENT AND TRADEMARK OFFICE
CERTIFICATE OF CORRECTION

PATENT NO. : 8,871,711 B2  
APPLICATION NO. : 13/129100  
DATED : October 28, 2014  
INVENTOR(S) : George Cotsarelis et al.

Page 1 of 1

It is certified that error appears in the above-identified patent and that said Letters Patent is hereby corrected as shown below:

In the Specification

In Column 1, Line 16, the terms "in whole or in part" should be deleted.

In Column 1, Line 17, the term "NIH/NIAMS" should be deleted.

In Column 1, Line 19, the terms "may have" should read "has".

Signed and Sealed this  
Twenty-first Day of February, 2017

Michelle K. Lee  
*Director of the United States Patent and Trademark Office*